United States Patent
Vizoso Piñeiro et al.

(10) Patent No.: US 12,214,000 B2
(45) Date of Patent: Feb. 4, 2025

(54) HUMAN UTERINE CERVICAL STEM CELL POPULATION AND USES THEREOF

(71) Applicant: GISTEM RESEARCH S.L., Gijon (ES)

(72) Inventors: Francisco José Vizoso Piñeiro, Gijon (ES); Román Pérez Fernández, Santiago de Compostela (ES); Noemí Eiró Díaz, Gijon (ES)

(73) Assignee: GISTEM RESEARCH S.L., Gijon (ES)

( * ) Notice: Subject to any disclaimer, the term of this patent is extended or adjusted under 35 U.S.C. 154(b) by 530 days.

(21) Appl. No.: 17/227,252

(22) Filed: Apr. 9, 2021

(65) Prior Publication Data

US 2021/0299184 A1    Sep. 30, 2021

Related U.S. Application Data

(62) Division of application No. 14/769,563, filed as application No. PCT/EP2014/053508 on Feb. 24, 2014, now abandoned.

(30) Foreign Application Priority Data

Feb. 22, 2013  (EP) .................... 13156348

(51) Int. Cl.
| | | |
|---|---|---|
| A61K 35/48 | (2015.01) | |
| C12N 5/071 | (2010.01) | |
| C12N 5/074 | (2010.01) | |
| C12N 5/077 | (2010.01) | |
| C12N 5/0775 | (2010.01) | |

(52) U.S. Cl.
CPC ............ *A61K 35/48* (2013.01); *C12N 5/0607* (2013.01); *C12N 5/0661* (2013.01); *C12N 5/0668* (2013.01); *C12N 5/0682* (2013.01); *C12N 2502/03* (2013.01); *C12N 2509/00* (2013.01)

(58) Field of Classification Search
CPC .... A61K 35/48; C12N 5/0607; C12N 5/0661; C12N 5/0668; C12N 5/0682; C12N 2502/03; C12N 2509/00
See application file for complete search history.

(56) References Cited

FOREIGN PATENT DOCUMENTS

| CN | 102229911 A | 11/2011 |
|---|---|---|
| WO | 2011042547 A1 | 4/2011 |

OTHER PUBLICATIONS

Pessina et al. Mesenchymal Stromal Cells Primed with Paclitaxel Provide a New Approach for Cancer Therapy. PLoS One (2011), 6(12), e28321. (Year: 2011).*
Allickson et al. Recent Studies Assessing the Proliferative Capability of a Novel Adult Stem Cell Identified in Menstrual Blood. The Open Stem Cell Journal (2011), v3, p. 4-10. (Year: 2011).
Baege, Astrid C., et al., "Cervical stem cells: Isolation, characterization, and potential role in human papillomavirus (HPV)-induced cervical carcinogenesis", Proceedings of the American Association for Cancer Research Annual Meeting, vol. 47, p. 938, (Apr. 2006), Abstract.
Dominici, et al., "Minimal criteria for defining multipotent mesenchymal stromal cells. The International Society for Cellular Therapy position statement", Crytotherapy vol. 8, 2006, 315-317.
Eggenhofer, et al., "The life and fate of mesenchymal stem cells", Frontiers in Immunolo!::iv, vol. 5, May 19, 2014, 1-6.
Lopez, Jacqueline, et al., "Human Papillomavirus Infections and Cancer Stem Cells of Tumors from the Uterine Cervix", The Open Virology Journal, vol. 6, (2012), 232-240.
Martens et al. Cytokeratin 17 and p63 are Markers of the HPV Target Cell, the Cervical Stem Cell. Anticancer Research (2004), v24 , p. 771-776. (Year: 2004).
Maruyama, T., et al., "Human uterine stem/progenitor cells: their possible role in uterine physiology and pathology", Reproduction vol. 140, No. 1, (Jul. 1, 2010), 11-22.
PCT International Search Report and Written Opinion mailed Apr. 4, 2014, PCT /EP2014/053508, 12 pages.
Song et al. In Vitro and In Vivo Characteristics of Stem Cells Derived from the Periodontal Ligament of Human Deciduous and Permanent Teeth. Tissue Engineering Part A (2012), 18(19), p. 2040-2051. (Year: 2012).
Sun, Xiaochun, et al., "Mesenchymal stem cells isolated from human uterine cervix cancer tissues", Cell Biology International vol. 35, No. 2, (Feb. 2011 ), 119-123.

* cited by examiner

*Primary Examiner* — Sean C. Barron
(74) *Attorney, Agent, or Firm* — WOMBLE BOND DICKINSON (US) LLP

(57) ABSTRACT

The present invention relates to a method for isolating stem cells comprising preparing a cell suspension from uterine cervix tissue, to the stem cells isolated by said method, and to the conditioned medium obtained from the culture of said stem cells. The invention also encompasses the use of said stem cells or conditioned medium for treating or preventing cancer, precancerous lesions, inflammatory diseases, autoimmune diseases, chronic pathologies or infectious diseases, diseases associated to tissue loss, or for use in diagnostic, prognostic or treatment of fertility disorders, as well as for cosmetic treatment.

4 Claims, 29 Drawing Sheets
Specification includes a Sequence Listing.

C

CD44-PE

CD117-PE

CD45-FITC

CD73-PE

CD133-PE

TRA1-81-FITC

A

B

A

B

A

B

C

D

A

| | +FBS | -FBS | +CM |
|---|---|---|---|
| | MDA-MB-231 cells | | |
| $G_0$-$G_1$ (%) | 51.4 ± 4.5 | 56.4 ± 2.5 | 65.6 ± 4.1 |
| S (%) | 10.9 ± 0.3 | 7.1 ± 1.9 | 9.3 ± 0.7 |
| $G_2$-M (%) | 37.6 ± 4.3 | 35.8 ± 0.6 | 25.0 ± 4.3 |

B

C

| | +FBS | -FBS | +CM |
|---|---|---|---|
| Annexin V - / PI - (%) | 85.2 ± 4.8 | 82.8 ± 4.0 | 61.5 ± 9.3 |
| Annexin V + / PI - (%) | 5.3 ± 1.2 | 9.3 ± 1.7 | 17.8 ± 9.7 |
| Annexin V + / PI + (%) | 5.7 ± 3.8 | 5.2 ± 1.4 | 16.7 ± 4.8 |
| Annexin V - / PI - (%) | 3.4 ± 1.7 | 2.4 ± 2.0 | 3.8 ± 3.6 |

MDA-MB-231 cells

D

E

A

B

C

D

E

F

A

B

C

HUMAN UTERINE CERVICAL STEM CELL POPULATION AND USES THEREOF

CROSS-REFERENCE TO RELATED APPLICATIONS

The present patent application is a divisional of U.S. patent application Ser. No. 14/769,563, filed Aug. 21, 2015, which is a national phase application of International Application No. PCT/EP2014/053508, filed Feb. 24, 2014, which claims priority to European Application No. 13156348.8, filed Feb. 22, 2013, the disclosures of which are incorporated herein by reference.

INCORPORATION BY REFERENCE

The content of the ASCII text file of the sequence listing named "Sequence_Listing_Patenin_ST25", which is 2 kb in size, was created on and electronically submitted via EFS-Web Apr. 9, 2021, is incorporated herein by reference in its entirety.

TECHNICAL FIELD OF THE INVENTION

The present invention relates to a method for isolating stem cells comprising preparing a cell suspension from uterine cervix tissue, to the stem cells isolated by said method, and to the conditioned medium obtained from the culture of said stem cells. The invention also encompasses the use of said stem cells or conditioned medium for treating or preventing cancer, inflammatory diseases, autoimmune diseases chronic pathologies or infectious diseases, as well as for cosmetic treatment. Therefore, the present invention relates to the field of stem cells and the therapeutic or cosmetic use thereof.

BACKGROUND ART

A stem cell is characterized by its ability to self-renew and to differentiate along multiple lineage pathways. A particularly promising type of adult stem cells for therapeutic applications is the so-called mesenchymal stem cells (MSCs). MSCs, also defined as multipotent mesenchymal stromal cells, are a heterogeneous population of cells that proliferate in vitro as plastic-adherent cells, have fibroblast-like morphology, form colonies in vitro and can differentiate into cells of the mesodermal lineage such as osteocytes, chondrocytes and adipocytes, as well as cells of other embryonic lineages.

Stem cells are thought to reside in a niche, which regulates the balance between stem cell self-renewal and tissue regeneration. The concept of a stem cell niche was originally described with reference to mammalian hematopoiesis in which the niche represented a specialized microenvironment housing the hematopoietic stem cell and assuring its continued existence. It was proposed that the support cells within the niche with their secretory products would interact with and govern stem cell behavior. In order to support stem cell activity, according to this model, conditions within the niche would be conducive to maintaining stem cell quiescence in the absence of any external activating cues but would promote proliferation and maturation of the progenitors should the need arise, and would also ensure self-renewal of the stem cell pool.

The presence of different populations of multipotent adult cells in soft tissues derived from the embryonic mesoderm has been reported by several authors. For example, it has been reported that multipotent cells can be obtained from skeletal muscle and other connective tissue of mammals, from human lipoaspirated tissue or from bone marrow [the so-called Multipotent Adult Progenitor Cells (MAPC)]. In principle, all these isolated cell populations could be used in the repair and regeneration of connective tissue in a similar fashion to the MSC of bone marrow. However, except for MAPC, none of these populations has been, until present, sufficiently characterized at the phenotype level. Therefore, although the presence of multipotent adult cells has been described in different connective tissues, in the current state of the art, it is not possible to identify and unequivocally distinguish between different multipotent cell types obtained from soft tissue, or to obtain a substantially pure population. Currently, phenotype characterization of stem cells comprises determination of markers such as cell surface receptors, among others; and the determination of their capacity for differentiation in vitro cultures. Each cell type has a certain combination of surface markers, that is, it has a certain profile of expression that characterizes that particular cell type, distinguishing it from others.

The ideal source of adult stem cells is one in which they can be obtained by an easy, non-invasive process and one that allows a sufficient number of cells to be isolated. In particular, a source should provide stem cells that can be easily isolated from a living subject without significant risks and discomfort and the source should allow a high yield to be obtained with minimal contamination from other cell types, without excessive cost of isolation and culture.

Although bone marrow (BM) has been the main source for the isolation of multipotent MSCs, adipose tissue is another source of this cell but the harvest of BM and adipose tissue is a highly invasive procedure. One alternative source is umbilical cord blood, which can be obtained by a less invasive method, without harm to the mother or infant. Other sources of MSCs were identified in a variety of other human adult tissues, including placenta, scalp tissue and intestinal stem cells. All cells isolated from BM, adipose tissue or umbilical cord blood (UCB) exhibited typical MSC characteristics: a fibroblastoid morphology, the formation of colony-forming-unit-fibroblasts (CFU-F), a multipotential differentiation capability, and the expression of a typical set of surface proteins. Whereas MSCs derived from the three sources expressed classic MSC marker proteins, it was observed significant differences concerning the expression of CD90, CD105, and CD106. Thus, MSCs could show different phenotype dependent of their source.

The process of obtaining bone marrow is painful and the yield is very low, a substantial increase in the number of cells being necessary by ex vivo expansion, to obtain clinically relevant amount. This step increases cost and makes the procedure time consuming, as well as increases the risk of contamination and loss of material. For these reasons, it would be very desirable to be able to isolate multipotent cells from mesenchymal tissues other than bone marrow. In particular, given their surgical accessibility, it would be convenient to be able to isolate cells from non-osteochondral mesodermal tissues such as, but not limited to, skin, fat and muscle tissue.

Thus, there is the necessity in the state of the art to provide an alternative source of stem cells by non-invasive and painless harvesting. In this sense, the uterus can be a source of stem cells. However, the uterus is a complex organ divided in different parts. Concretely, the human uterus is a fibromuscular organ that can be divided into the upper muscular uterine corpus and the lower fibrous cervix, which extends into the vagina. The corpus uteri is divided into the fundus and the lower uterine segment (or isthmus), which lies approximately at the level of the course of the uterine artery and the internal os of the cervix. The cervix is a narrow cylindrical passage which connects at its lower end with the vagina and at its upper end, the cervix widens to form the lower uterine segment (isthmus); the lower uterine segment in turn widens into the uterine fundus (FIG. 18). The lower end of the cervix that can be seen from inside the vagina during a gynecologic examination is known as the ectocervix. An opening in the center of the ectocervix, known as the external os, opens to allow passage between the uterus and vagina. The endocervix surround the endocervical canal, which is a tunnel through the cervix, from the external os into the uterus (FIG. 19). The overlapping border between the endocervix and ectocervix is called the transformation zone. The transformation zone is the region where the stem cells of the invention are, preferably collected.

Arthur Worth Ham, a prominent Canadian histologist, has described in his textbook "*Histology*" (Ham, A. W. and Cormack, D. H. Ham's Histology, 9th ed. Philadelphia: Lippincott, 1987), considered by many practitioners an indispensable reference, the different tissue layer of the corpus uteri and cervix. The human corpus uteri consists of the following three tissue layers: 1) the inner layer, called the endometrium, is the most active layer and responds to cyclic ovarian hormone changes; the endometrium is highly specialized and is essential to menstrual and reproductive function (endometrial stem cells derived from this tissue layer); 2) the middle layer, or myometrium, makes up most of the uterine volume and is the muscular layer, composed primarily of smooth muscle cells (myometrial stem cells derived from this tissue layer); and 3) the outer layer of the uterus, the serosa or perimetrium, is a thin layer of tissue made of epithelial cells that envelop the uterus. However, both, cervix wall and the membrane lining the canal have different characteristics than the corpus uteri. Indeed, the cervix wall is mainly constituted by connective tissue. The cervix is composed by an inner lining known as the mucous membrane, which is composed of thin, flat, scaly cells called squamous cells and an outer lining known as the serous membrane (slippery covering). In addition, the wall of the portion of the corpus uteri that joins the cervix, called lower uterine segment or isthmus, is primarily composed of smooth muscle. Therefore, the histology and, then, the function of these two parts of the uterus (corpus uteri, including the lower uterine segment, and cervix) are different.

The international application WO2011/042547 discloses a method to provide stem cells from myometrial tissue specifically from an area above the cervix, called corpus uteri, which include the fundus and the lower uterine segment. Moreover, the authors mentioned that myometrial explants were taken from the lower uterine segment of the corpus uteri by exfoliation. As it has been described above the lower uterine segment is the upper end of the cervix and considered part of the corpus uteri which is anatomically and histologically different to cervix. However, it is classically known that the wall of the lower uteri corpus is mainly composed by myometrial tissue because the endometrial layer is reduced to this level. Nevertheless, the external wall of the cervix is mainly composed by connective tissue. Therefore, it is not possible to obtain myometrial tissue by superficial cytological sampling from uterine cervix. Therefore, the biological material is obtained by invasive methods, such as biopsy, myometrial tissue pieces, myometrial explants or as uterine exfoliation, which need a high grade of exfoliation to achieve myometrium. Consequently, tissue samples were trimmed of endometrial, serosal, fat and fibrous tissue prior to use for isolate myometrial precursors. The stem cell population described in the international application WO2011/042547 expresses surface markers such as CD31, CD34 and HLA-DR which are surface markers from haematopoietic lineage. On the contrary, the mesenchymal stem cells, did not express these haematopoietic markers.

Baege Astrid C and coworkers (Baege Astrid C et al. Proc Amer Assoc Cancer Res Annual Meeting. Vol 47, 2006: 938) discloses the isolation of putative epithelial stem cells, different to mesenchymal stem cell. It is important to note that the cells population discloses herein was associated with a potential role in human papillomavirus-induced cervical carcinogenesis.

Moreover, Maruyama T et al (Maruyama T et al. Reproduction; 2010; 140:11-22) discloses the role of endometrial and myometrial stem/progenitor cells in the physiology and pathology of the uterus, however, this document does not mention to mesenchymal cervical stem cells. As it has been mentioned above, the myometrium is the middle layer, of the corpus uteri, it makes up most of the uterine volume and is the muscular layer, composed primarily of smooth muscle cells.

On the other hand, Lopez J et al (López J et al. Open Virol J. 2012; 6: 232-240) and Xiaochun S et al (Xiaochun S et al. Cell Biol Int. 2011; 35:119-123) discloses stem cells which were isolated and identified from human uterine cancer. The disadvantage of these stem cells is their contribution to tumor growth. In this sense, it has been described (Ramasamy R et al., Leukemia, 2007) that mesenchymal stem cells were components of cancer stem cells niches and consequently play a crucial role in supporting tumor cell growth. Therefore, stem cells isolated from cancer tissue show differences in tumor properties and surely in other properties, than stem cells isolated from normal tissues.

DETAILED DESCRIPTION OF THE INVENTION

The authors of the present invention have discovered that the uterine cervix tissue can be used as source of stem cells. The cells isolated from this tissue, called uterine cervical stem cells (UCESC), show a higher anti-inflammatory activity, anti-tumor capacity, antimicrobial activity and growth rate than other mesenchymal stem cells isolated from other tissues, and are capable of keeping their functionality and a stable karyotype for at least 10 cell passages. Additionally, the new source of stem cells allows the isolation of mesenchymal stem cells by a non-invasive and painless method since said tissue can be obtained just by exfoliating said organ during a routine gynaecological examination.

Based on this new source of stem cells and the cells obtained from it, the authors of the present invention have developed the following inventive aspects which will be disclosed in detail below.

Method of the Invention

As explained above, the authors of the present invention have discovered that the uterine cervix tissue can be used as source of stem cells, preferably, non-cancerous uterine cervix tissue.

Thus, in an aspect, the present invention relates to a method for isolating stem cells, hereinafter the "method of the invention", comprising:

(a) preparing a cell suspension from uterine cervix tissue,
(b) recovering the cells from said cell suspension,
(c) incubating said cells in a suitable cell culture medium under conditions which allow cells to proliferate, and
(d) selecting the stem cells.

Steps (a)-(d) can be carried out by conventional techniques known by those skilled in the art. An additional advantage of this new source of stem cells is that it allows obtaining stem cells from the animal body in a non-invasive and painless way.

In the context of the present invention, the term "non-invasive" refers to a process where the skin is not broken and the body cavities are not probed using tools which go beyond the usual tools for gynaecological examination. In the context of the present invention, the term "painless" refers to a process which does not cause physical pain. Therefore, the method of the invention is a non-invasive and painless method for isolating stem cells since the source from which said stem cells are isolated is uterine cervix.

Thus, in a first step [step (a)], the method of the invention comprises preparing a cell suspension from uterine cervix tissue.

The term "uterine cervix tissue" refers to the tissue coming from the uterine cervix, i.e. the organ which separates the body and cavity of the uterus from the vagina. The uterine cervix is a narrow cylindrical passage which connects at its lower end with the vagina and at its upper end, the cervix widens to form the lower uterine segment (isthmus); the lower uterine segment in turn widens into the uterine fundus (FIG. 18). The lower end of the cervix that can be seen from inside the vagina during a gynecologic examination is known as the ectocervix. An opening in the center of the ectocervix, known as the external os, opens to allow passage between the uterus and vagina. The endocervix surround the endocervical canal, which is a tunnel through the cervix, from the external os into the uterus (FIG. 19). The overlapping border between the endocervix and ectocervix is called the transformation zone. The transformation zone is the region where the stem cells of the invention are, preferably collected.

The uterine cervix tissue can be obtained by any conventional method known by the skilled person in the art for removing tissues from the animal body, both invasive, such as biopsy, and non-invasive methods, such as exfoliation of the uterine cervix. Preferably, the uterine cervix tissue is obtained by exfoliating the uterine cervix during a routine gynaecological examination which supposes a non-invasive and painless way of obtaining stem cells. The uterine cervix tissue can be obtained from any suitable mammal, e.g. a cow, a sheep, a pig, a dog, a cat, a horse, a primate, etc., preferably humans.

Once the uterine cervix tissue is obtained, the tissue is, preferably, washed before being processed to separate the cells of the invention from the remainder of the material. In a protocol, the uterine cervix tissue is maintained in a physiologically-compatible saline solution (e.g., phosphate buffered saline (PBS)) or in serum-free medium. Due to the special characteristics of the uterine cervix tissue, in a particular embodiment, the step (a) of the method of the invention comprises enzymatically disaggregating the cervical mucus. Any enzyme capable of disaggregating the cervical mucus can be used in the present method (e.g., collagenase, dispase, trypsin, etc.). The amount and duration of the enzymatic treatment will vary, depending on the conditions employed, but the use of such enzymes is generally known in the art. Alternatively or in conjunction with such enzymatic treatment, the cervical mucus can be degraded using other treatments, such as mechanical agitation, sonic energy, thermal energy, etc. If degradation is accomplished by enzymatic methods, it is desirable to neutralize the enzyme following a suitable period, to minimize deleterious effects on the cells.

The degradation step typically produces a slurry or suspension of aggregated cells and a fluid fraction containing generally free stromal cells (e.g., red blood cells, endothelial cells, fibroblast cells, and stem cells). The next stage [step (b)] in the method is to recover the cells from said cell suspension, which means separate the aggregated cells from the rest. This can be accomplished by centrifugation, which forces the cells into a pellet covered by a supernatant. The supernatant then can be discarded and the pellet suspended in a physiologically-compatible fluid. Moreover, the suspended cells typically include erythrocytes, and in most protocols it is desirable to lyse them. Methods for selectively lysing erythrocytes are known in the art, and any suitable protocol can be employed (e.g., incubation in a hyper-or hypotonic medium, by lysis using ammonium chloride, etc.). Of course, if the erythrocytes are lysed, the remaining cells should then be separated from the lysate, for example by filtration, sedimentation, centrifugation or density fractionation. The suspended cells can be washed, re-centrifuged, and resuspended one or more successive times to achieve greater purity. Alternatively, the cells can be separated on the basis of cell surface marker profile or on the basis of cell size and granularity.

Following the recovery of the cells from the cell suspension, the cells are cultured in a suitable cell culture medium under conditions which allow the cells to proliferate [step (c)]. Preferably, the cells will be cultured without differentiation, using a suitable cell culture media, at the appropriate cell densities and culture conditions. Thus, cells are cultured without differentiation on a solid surface, in the presence of a suitable cell culture medium [e.g. DMEM, DMEM-F12, alpha-MEM, RPMI, typically supplemented with 5-25% (e.g. 20%) of a suitable serum, such as fetal bovine serum, fetal calf serum, newborn calf serum, calf serum, porcine serum, sheep serum, horse serum, human serum or human serum, factors, amino acids, etc.], and incubated under conditions which allow cells to proliferate. The culture conditions, i.e., pH, temperature, etc., are common general knowledge for the skilled person in the art. Preferably, the cells are culture on a solid surface and under conditions which allow cells to adhere to said solid surface and proliferate.

As used herein, the term "solid surface" refers to any material that allows the cells of the invention to adhere. For example, said material is a plastic material, such as Petri dishes or cell culture flasks, treated to promote the adhesion of mammalian cells to its surface, for example commercially available polystyrene plates optionally coated with gelatin, fibronectin, poly-D-Lysine or other reagents. After incubation, cells are washed in order to remove non-adhered cells and cell fragments.

Once the cells proliferate, these may be maintained in culture in the same medium and under the same conditions until they reach the adequate confluence, typically, about 80% cell confluence, with replacement of the cell culture medium when necessary. After reaching the desired cell confluence, the cells can be expanded by means of consecutive passages using a detachment agent such as trypsin and seeding onto a bigger cell culture surface at the appropriate cell density (usually 2,000-10,000 cells/cm$^2$). Thus, cells are then passaged at least two times in such medium without differentiating, while still retaining their developmental phenotype. More preferably, the cells can be passaged at least 10 times (e.g. at least 15 times or even at least 20 times) without losing developmental phenotype. Typically, the cells are plated at a desired density such as between about 100 cells/cm$^2$ to about 100,000 cells/cm$^2$ (such as about 500 cells/cm$^2$ to about 50,000 cells/cm$^2$, or, more particularly, between about 1,000 cells/cm$^2$ to about 20,000 cells/cm$^2$). If plated at lower densities (e.g. about 300 cells/cm$^2$), the cells can be more easily clonally isolated. For example, after a few days, cells plated at such densities will proliferate into a homogeneous population.

Finally, the method comprises selecting the stem cells [step (d)]. The stem cells can be selected by any conventional method, such as immunocytochemistry (ICC), flow cytometry, etc. The immunocytochemistry is a technique used to assess the presence of a specific protein or antigen in cells (cultured cells, cell suspensions) by use of a specific antibody, which binds to it, thereby allowing visualization and examination under a microscope. As the skilled person known, the cells to be stained can be attached to a solid support to allow easy handling in subsequent procedures, which can be achieved by several methods: adherent cells may be grown on microscope slides, coverslips, an optically suitable plastic support, etc. On the other hand, the flow cytometry is a laser based, biophysical technology employed in cell counting, sorting, biomarker detection and protein engineering, by suspending cells in a stream of fluid and passing them by an electronic detection apparatus. A specialized type of flow cytometry is the fluorescence-activated cell sorting or FACS. It provides a method for sorting a heterogeneous mixture of biological cells into two or more containers, one cell at a time, based upon the specific light scattering and fluorescent characteristics of each cell. These methods are widely known by the skilled person in the art as well as the cell markers, for example, cell surface markers, to be detected in order to identify or select stem cells.

If desired, any of the steps and procedures for isolating the stem cells can be performed manually. Alternatively, the process of isolating such cells can be facilitated and/or automated through one or more suitable devices, examples of which are known in the art. Example 1 describes in a detailed manner the isolation of the cells of the invention from human uterine cervix tissue. As a result of the method of the invention, a homogeneous cell population of uterine cervical stem cells is obtained.

Thus, in particular embodiment, the isolated stem cells:
(a) express the cell markers CD29, CD44, CD73, CD90, CD105, vimentin, cytokeratin (CKAE1AE3), Klf4, Oct4 and Sox-2, and
(b) do not express at least one cell marker selected from the group consisting of desmin, actin HHF35, β-catenin, p63, E-cadherin, CD117, CD133, HLA-DR, TRA1-81, CD45, CD34 and CD31.

Confirmation of the phenotype of interest can be carried out by using conventional means. Cell markers, for example, cell-surface markers, can be identified by any suitable conventional technique, usually based on a positive/negative selection, for example, monoclonal antibodies against cell-surface markers, whose presence/absence in the cells has to be confirmed, can be used, although other techniques can also be used.

Monoclonal antibodies against CD29, CD44, CD73, CD90, CD105, vimentin, cytokeratin (CKAE1AE3), Klf4, Oct4 and Sox-2 cell markers are used in order to confirm the presence of said markers in the selected cells (or detectable expression levels of said markers), and monoclonal antibodies against at least 1, 2, 3, 4, 5, 6, 7, 8, 9, 10, 11 or 12 of the cell markers selected from the group consisting of desmin, actin HHF35, pi-catenin, p63, E-cadherin, CD117, CD133, HLA-DR, TRA1-81, CD45, CD34 and CD31 are used in order to confirm the absence thereof. Said monoclonal antibodies are known, commercially available or can be obtained by a skilled person in the art by conventional methods.

In another particular embodiment, the isolated stem cells, further shows (a) a proliferating rate from 0.4 to 2.1 doublings per 24 hours in growth medium,
(b) a fibroblast-like morphology,
(c) a stable karyotype for at least 10, preferably 20 cell passages,
(d) capacity to grow in monolayer and to adhere to a substrate,
(e) capacity to be differentiated into endodermal, ectodermal or mesodermal lineages, preferably, an adipogenic, osteogenic, neural or myocytic cell linage,
(f) a non tumorigenic capacity and/or
(g) capacity to form spheres.

In another particular embodiment, the method discloses herein it is characterized by the uterine cervix tissue is a non-cancerous uterine cervix tissue, preferably a non-cancerous mammalian uterine cervix tissue and more preferably, a human non-cancerous uterine cervix tissue.

The term "non-cancerous uterine cervix tissue" refers to the uterine cervix tissue having a morphology different from normal uterine cervix tissue, such as cancer or malignant tissue.

Detailed disclosure of the stem cells obtained by the method of the invention can be found below.

In view of the above-mentioned, the skilled person in the art understands that the use of isolated uterine cervix tissue, preferably, a non-cancerous isolated uterine cervix tissue, i.e. tissue removed from its original environment (uterine cervix) and thus altered "by the hand of man" from its natural state, for obtaining uterine cervix stem cells, preferably, non-cancerous uterine cervix stem cells, is contemplated as another aspect of the present invention.

Cell and Conditioned Medium of the Invention

As consequence of putting into practice the method of the invention (depicted above) an uterine cervix stem cell is obtained.

Thus, in another aspect, the present invention relates to an isolated uterine cervix stem cell, hereinafter "cell of the invention", wherein said cell:
(a) expresses cell markers CD29, CD44, CD73, CD90, CD105, vimentin, cytokeratin (CKAE1AE3), Klf4, Oct4 and Sox-2, and
(b) does not express at least one cell marker selected from the group consisting of desmin, actin HHF35, β-catenin, p63, E-cadherin, CD117, CD133, HLA-DR, TRA1-81, CD45, CD34 and CD31.

In the context of the present invention, the term "isolated" refers to a cell isolated from the human or animal body, which is substantially free of one or more cells that are associated with said cell in vivo or in vitro.

The stem cell obtained by the method of the invention expresses cell markers CD29, CD44, CD73, CD90, CD105, vimentin, cytokeratin (CKAE1AE3), Klf4, Oct4 and Sox-2. In the context of the present invention, it is considered that a cell express a cell marker when there is a "significant expression" of the cell marker analysed. As used herein, the expression "significant expression" means that, in a cell population comprising the cell of the invention, more than 10%, preferably 20%, 30%, 40%, 50%, 60%, 70%, 80%, 90% or all of the cells show a signal for a specific cell marker in flow cytometry or immunocytochemistry above the background signal using conventional methods and apparatus (for example a Beckman Coulter Epics XL FACS system or Dako Autostainer Plus system used with commercially available antibodies and standard protocols known in the art). For cytokeratin (CKAE1AE3) a "significant expression" means the presence of a focal expression. The background signal is defined as the signal intensity given by a non-specific antibody of the same isotype as the specific antibody used to detect each surface marker in conventional FACS analysis. Thus for a marker to be considered "present" in the cell or positive, the specific signal observed is stronger than 10%, preferably 20%, 30%, 40%, 50%, 60%, 70%, 80%, 90%, 500%, 1000%, 5000%, 10000% or above, than the background signal intensity using conventional methods and apparatus (for example a Beckman Coulter Epics XL FACS system used with commercially available antibodies and standard protocols known in the art).

Additionally, the cell of the invention does not express at least one cell marker selected from the group consisting of desmin, actin HHF35, β-catenin, p63, E-cadherin, CD117, CD133, HLA-DR, TRA1-81, CD45, CD34 and CD31, i.e., they are negative for at least 1, 2, 3, 4, 5, 6, 7, 8, 9, 10, 11 or 12 of the following markers desmin, actin HHF35, R-catenin, p63, E-cadherin, CD117, CD133, HLA-DR, TRA1-81, CD45, CD34 and CD31.

As used herein, "negative" with respect to cell markers means that, in a cell population comprising the cell of the invention, less than 10%, preferably 9%, 8%, 7%, 6%, 5%, 4%, 3%, 2%, 1% or none of the cells show a signal for a specific cell marker in flow cytometry or immunocytochemistry above the background signal, using conventional methods and apparatus (for example a Beckman Coulter Epics XL FACS system or Dako Autostainer Plus system used with commercially available antibodies and standard protocols known in the art).

Advantageously, as shown in the examples, the cell of the invention exhibits other useful characteristics. Thus, in a particular embodiment, the cell of the invention further shows at least one, preferably all, of the following features:
  (a) A proliferating rate from 0.4 to 2.1 doublings per 24 hours in growth medium.
    The high grow rate of the cells of the invention allows quickly and in huge amounts the production of stem cells or conditioned medium. This offers the possibility of (i) carrying out a great number of experiments in order to analyze the biology and uses of these stem cells (this is complicated with the mesenchymal stem cells currently known in the state of the art which show a low grow rate); (ii) a fast tissue regeneration since a high number of stem cell can be obtained in a short period of time; and (iii) quickly obtaining a huge amount of stem cell for its use in anti-inflammatory, anti-tumoral and anti-infectious therapies.
  (b) A fibroblast-like morphology.
  (c) A stable karyotype for at least 10, preferably, 20 cell passages, i.e. the cells maintain over a time the number and appearance of chromosomes in the nucleus.
    This allows ensuring the stem cells functionality for a long period of time, being possible to produce a reproducible and effective medicament along stem cell the passages.
  (d) Capacity to grow in monolayer and to adhere to a substrate.
  (e) Capacity to be differentiated into endodermal, ectodermal or mesodermal cell lineage, preferably, an adipogenic, osteogenic, neural or myocytic cell linage. The capacity of the selected cells to differentiate into at least one of said lineages can be assayed by conventional methods known in the art and common practice for the skilled person.
  (f) A non-tumorigenic capacity, i. e. they do not present an altered behaviour or proliferative phenotype which gives rise to a tumour cell.
  (g) Capacity to form spheres, i.e. capacity to form a group or a colony of cells in a suspension culture, highly proliferative in presence of mitogenic factors (mainly, epidermal growth factor (EGF) and fibroblast growth factor (FGF)).
    This capacity represents a potential way to get in vitro neural progenitor cell-like.

In a particular embodiment, the cell of the invention is from a human, preferably, from a human in a non-menstrual phase.

The skilled person in the art understands that the cell of the invention may be part of a cell population. Therefore, in another aspect, the invention relates to an isolated cell population comprising the cell of the invention, hereinafter "cell population of the invention".

The term "isolated" applied to a cell population refers to a cell population, isolated from the human or animal body, which is substantially free of one or more cell populations that are associated with said cell population in vivo or in vitro.

The cells and cell population provided by the instant invention can be clonally expanded, if desired, using a suitable method for cloning cell populations. For example, a proliferated population of cells can be physically picked and seeded into a separate plate (or the well of a multi-well plate). Alternatively, the cells can be subcloned onto a multi-well plate at a statistical ratio for facilitating placing a single cell into each well. Of course, the cells can be cloned by plating them at low density (e. g. in a Petri dish or other suitable substrate) and isolating them from other cells using devices such as cloning rings. The production of a clonal population can be expanded in any suitable culture medium. In any event the isolated cells can be cultured to a suitable point when their developmental phenotype can be assessed.

Further to the uterine cervix stem cell, the present invention also contemplates the conditioned medium obtained from the culture of said cell. As the skilled person understands, the conditioned medium can be used in the place of the cells themselves because this conditioned medium provides the many compounds secreted by the cells of the invention.

Thus, in another aspect, the invention relates to a conditioned medium, hereinafter "conditioned medium of the invention", obtained by a method comprising:
  (a) Incubating the isolated stem cell of the invention or the cell population of the invention, and
  (b) Removing the cells from the culture medium.

As used herein, the term "conditioned medium" refers to the spent media harvested from cultured cells, i.e. from the cultured cells of the invention (uterine cervix stem cells). The conditioned medium contains metabolites, growth factors, and extracellular matrix proteins secreted into the medium by the cultured cells.

Examples of each component include, but not limiting to, metabolites such as glucose, amino acids, nucleosides, etc.; growth factors, such as interleukins, EGF (epidermal growth factor), PDGF (platelet-derived growth factor), etc.; and matrix proteins such as collagen, fibronectin, various proteoglycans, etc.

The conditioned medium of the invention is produced by culturing the isolated cell of the invention under suitable conditions and for a time sufficient for the cells to secrete the active compounds into the medium. Suitable cell culture medium for culturing the cells of the invention comprises, for example, DMEM, DMEM-F12 or alpha-MEM, RPMI, typically supplemented with 5-25% (e.g. 20%) of a suitable serum, such as fetal bovine serum, fetal calf serum, newborn calf serum, calf serum, porcine serum, sheep serum, horse serum, human serum or human serum, factors, amino acids, etc. The culture conditions, i.e., pH, temperature, etc., are common general knowledge for the skilled person in the art. On the other hand, the culture of the cells can be carried out using a bioreactor, allowing to both managing a high volume of medium and a suitable controlled environment for the cells. Bioreactors are widely known in the state of the art and its use is routine for the skilled person.

After culture, the medium is then processed to remove the cells. This may be done by any conventional method, for example, decantation, centrifugation, filtration etc. Then, the supernatant is collected as conditioned medium and kept at 4° C., −20° C., −80° C., in liquid nitrogen or another condition that can conserved its functionality such as, but not limiting, freeze-drying, lyophilization or cryodesiccation or it can be used immediately. Conditioned medium can be produced or treated to be concentrated o diluted. In addition, all or part of the conditioned medium composition can be synthesized.

Uses of the Cell of the Invention

Once the cell of the invention is isolated, both the cell and the conditioned medium obtained from it can be use for manufacture a pharmaceutical composition.

Thus, in another aspect, the invention relates to a pharmaceutical composition comprising an isolated stem cell, a cell population, or the conditioned medium of the invention, hereinafter "pharmaceutical composition of the invention", and an acceptable pharmaceutically carrier and/or an adjuvant.

The pharmaceutical composition of the invention comprises a prophylactically or therapeutically effective amount of a cell of the invention, a cell population, or the conditioned medium of the invention. Thus, the term "prophylactically" or "therapeutically effective amount" refers to the amount of agent capable of developing the therapeutic action determined by their pharmacological properties. It is calculated to produce the desired effect and generally will be determined, among other things, by combining the characteristics of compounds and patients, including age, state of the patient, severity of the disturbance or disorder, and route and frequency of the administration.

The term "pharmaceutically acceptable carrier" means that the carrier is approved by a regulatory agency of the Federal or a state government or listed in the U.S. Pharmacopeia, or European Pharmacopeia, or other generally recognized pharmacopeia for use in animals, and more particularly in humans. The term "carrier" refers to a diluent, adjuvant, excipient, or vehicle with which the therapeutic agent is administered. The composition, if desired, can also contain minor amounts of pH buffering agents. Examples of suitable pharmaceutical carriers are described in "Remington's Pharmaceutical Sciences" by E. W. Martin ($18^{th}$ edition, Mack Publishing Co.). Such compositions will contain a prophylactically or therapeutically effective amount of the cell of the invention, or a cell population of the invention preferably in purified form, or a conditioned medium of the invention, together with a suitable amount of carrier so as to provide the form for proper administration to the subject.

The formulation should suit the mode of administration. Preferably, the pharmaceutical compositions are sterile and in suitable form for administration to a subject, preferably an animal subject, more preferably a mammalian subject, and most preferably a human subject.

The pharmaceutical composition of the invention may be in a variety of forms. These include, for example, solid, semi-solid, and liquid dosage forms, such as lyophilized preparations, liquids solutions or suspensions, injectable and infusible solutions, etc. The preferred form depends on the intended mode of administration and therapeutic application.

The administration of the cell or the cell population or the conditioned medium of the invention, or the pharmaceutical composition comprising same, to the subject in need thereof can be carried out by conventional means. Preferably, said cell or cell population is administered to the subject by a method which involves transferring the cells to the desired tissue, either in vitro or in vivo, to the animal tissue directly. The cell or the conditioned medium can be transferred to the desired tissue by any appropriate method, which generally will vary according to the tissue type. For example, cells can be seeded onto the desired site within the tissue to establish a population, etc. Cells or conditioned medium can be transferred to sites in vivo using devices such as catheters, trocars, cannulae, stents, suture thread (which can be seeded with the cells or soaked in conditioned medium), etc.

As it is shown in the examples, the cell of the invention or the conditioned medium of the invention can be used for preventing, treating or ameliorating one or more symptoms associated with disorders in which modulation of a subject's immune system is beneficial, including, but not limited to, inflammatory disorders, autoimmune diseases, immunologically mediated diseases including rejection of transplanted organs and tissues, chronic pathologies and infectious diseases. Further, due to the anti-tumor capacity, they can be also used for the treatment or prevention of cancer. In addition, due to their capacity to regenerate or stimulate tissue regeneration (regenerative medicine), they can be used in wound healing or other processes associated with tissue destruction.

In addition, due to their capacity to regenerate or stimulate tissue regeneration (regenerative medicine), they can be used in wound healing or other processes associated with tissue destruction. Additionally, due to its capacity to secrete substances to the endocervical mucus (which aid the spermatozoa to pass the uterine cervical canal and to reach the ovum), they can be used in fertilization process. As can be seen from the examples, the cells or the conditioned medium of the invention modulate the characteristics of fresh ejaculate and capacitated spermatozoa, helping in the selection of suitable germ cells for fertilization process.

Thus, in another aspect, the present invention relates to the cell, the cell population, the conditioned medium or the pharmaceutical composition of the invention for use as a medicament.

In another aspect, the present invention relates to the cell, the cell population, the conditioned medium or the pharmaceutical composition of the invention for use in the treatment or prevention of cancer, inflammatory diseases, autoimmune diseases, chronic pathologies, infectious diseases, diseases with tissue loss/destruction, or for use in diagnostic, prognostic or treatment of fertility disorders.

As used herein, "treatment," "treat," or "treating," refers to: (a) preventing the disease or condition from occurring in a subject which may be predisposed to the disease or condition but has not yet been diagnosed as having it; (b)

inhibiting the disease or condition, i.e., arresting its development; (c) relieving and or ameliorating the disease or condition, i.e., causing regression of the disease or condition; or (d) curing the disease or condition, i.e., stopping its development or progression. The population of subjects treated by the stem cell, the cell population, the conditioned medium or the pharmaceutical composition of the invention includes subjects suffering from the undesirable condition or disease, as well as subjects at risk for development of the condition or disease. In the present invention, the diseases to be treated are selected from cancer, precancerous lesions, an inflammatory disease, an autoimmune disease, an immunologically mediated disease including rejection of transplanted organs and tissues, a chronic pathology and an infectious disease; diseases with tissue destruction or tissue loss and fertility disorders.

The terms "disorder" and "disease" are used interchangeably to refer to a condition in a subject.

The term "cancer" refers to a class of disease caused by a failure of the controls that normally govern cell proliferation, differentiation and cell survival, giving rise to cells that undergo malignant transformation (also called cancer cells or tumor cells), invading the surrounding tissue (and forming a malignant tumor), and which may ultimately migrate to other sites in the body to establish secondary tumors in a process called metastasis. Further, in the context of the present invention, the term "tumor" refers to abnormal tissue masses, and includes both benign and malignant masses. The benign tissue masses can also be treated with the cells, the cell population, the conditional medium or the pharmaceutical composition of the invention.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, supratentorial primitive neuroectodeimal tumors, visual pathway and hypothalamic glioma, breast cancer, bronchial adenomas/carcinoids, carcinoid tumor, gastrointestinal cancer, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, uterine sarcoma, uterine corpus cancer, vaginal cancer, vulvar cancer, and Wilm's Tumor.

The term "precancerous lesion" refers to lesions that exhibit histologic changes which are associated with an increased risk of cancer development.

The term "inflammatory disease" refers to a condition in a subject characterized by inflammation, e.g. chronic inflammation. Illustrative, non-limiting examples of inflammatory disorders which can be treated with the cell, the cell population, the conditioned medium or the pharmaceutical composition of the invention include, but not limited to, rheumatoid arthritis (RA), Inflammatory Bowel Disease (IBD), asthma, encephalitis, chronic obstructive pulmonary disease (COPD), inflammatory osteolysis, allergic disorders, septic shock, pulmonary fibrosis (e.g. idiopathic pulmonary fibrosis), inflammatory vacuhtides (e.g. polyarteritis nodosa, Wegner's granulomatosis, Takayasu's arteritis, temporal arteritis, and lymphomatoid granulomatosus), post-traumatic vascular angioplasty (e.g. restenosis after angioplasty), undifferentiated spondyloarthropathy, undifferentiated arthropathy, arthritis, inflammatory osteolysis, chronic hepatitis and chronic inflammation resulting from chronic viral or bacteria infections.

The term "autoimmune disease" refers to a condition in a subject characterized by cellular, tissue and/or organ injury caused by an immunologic reaction of the subject to its own cells, tissues and/or organs. Illustrative, non-limiting examples of autoimmune diseases which can be treated with the cell, the cell population, the conditioned medium or the pharmaceutical composition of the invention include, alopecia areata, ankylosing spondylitis, antiphosphohpid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, Meniere's disease, mixed connective tissue disease, multiple sclerosis, type 1 or immune-mediated diabetes mellitus, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, sarcoidosis, scleroderma, progressive systemic sclerosis, Sjogren's syndrome, Good pasture's syndrome, stiff-man syndrome, systemic lupus erythematosus, lupus erythematosus, takayasu arteritis, temporal arteritis/giant cell arteritis, ulcerative colitis, uveitis, vascuhtides such as dermatitis herpetiformis vasculitis, vitiligo, Wegener's granulomatosis, etc.

The term "chronic pathology" refers to a condition in a subject characterized by a long duration disease, stable or with a slow progression, constantly present or go into remission and periodically relapse. Illustrative, non-limiting examples of chronic diseases which can be treated with the cell, the cell population, the conditioned medium or the pharmaceutical composition of the invention include cardiovascular disease, heart disease, stroke, cancer, chronic respiratory diseases such as, but not limited to asthma or chronic obstructive pulmonary disease, diabetes, arthrosis, obesity, HIV/AIDS, dental cavities, periondontal disease, chronic ear infections, glaucoma and chronic viral or bacterial infection The term "infectious disease" refers to a condition in a subject characterized by the presence in the organism of a pathogenic microorganism, such as, bacteria, viruses, parasites or fungi. Illustrative, non-limiting examples of infectious diseases which can be treated with the cell, the cell population, the conditioned medium or the pharmaceutical composition of the invention include influenza, avian influenza, HIV/AIDS, legionellosis, sepsis, tuberculosis, buruli ulcer, trypanosomiasis, haemorrhagic fever (e.g. marburg haemorrhagic fever, ebola haemorrhagic fever or dengue haemorragic fever), hepatitis (e.g. hepatitis A, hepatitis B, hepatitis C), meningitis (e.g. meningococcal meningitis), cholera, yellow fever, malaria, leprosy.

The term "subject" in the above-mentioned definitions refers to any animal, including, but not limited to, mammals, preferably primates, more preferably humans. Thus, the isolated stem cell, the cell population, the conditioned medium or the pharmaceutical composition of the invention can be used in the treatment of any animal suffering from the above-mentioned diseases.

The term "tissue destruction" or "tissue loss" refers to a disease in which (a) a percentage of the structure's mass is removed, or b) the internal pattern and numbers of cells comprising the structure are damaged or killed while some vestigal cells and/or pattern remains. Examples of diseases with tissue destruction or tissue loss are selected from: ocular surface diseases as dry eye disease, corneal wound; or retinal diseases as age macular degeneration, retinal dystrophies-degenerations; or optic neuropathies, glaucoma, uveitis; or skin diseases, heart diseases, kidney diseases, or central nervous system, Alzheimer disease, amyotrophic lateral sclerosis or spinal muscular atrophy.

The term "fertility disorders" refers to problems to conceive a child due to problems related to the ovulation, including, but not limited to, poor egg quality, failure to ovulate through hormonal deficiency or imbalance, irregular ovulation and Polycystic Ovary Syndrome (PCOS); or to problems related to the sperm, including, but not limited to, abnormal sperm, insufficient sperm or low motility. Therefore, the cell, the cell population, the conditioned medium or the pharmaceutical composition of the invention can be used to treat a fertility disorders both in men and women.

The term "germ cells" refers to a reproductive cell such as a spermatocyte or an oocyte, or a cell that will develop into a reproductive cell.

The term "suitable germ cells" refers to gametes which, after a fertilization process, render a zygotes. Assays for determining if gametes are able to render a zygotes are known form the state of the art, and they are routine practice for the skilled person.

The present invention also contemplates the cell, the cell population, the conditioned medium or the pharmaceutical composition of the invention for use in a combination therapy for the prevention or treatment of cancer, precancerous lesions, inflammatory diseases, autoimmune diseases, chronic pathologies, infectious diseases, diseases associated to tissue loss, or for use in diagnostic, prognostic or treatment of fertility disorders.

The term "combination therapy" refers to the use of the cell, the cell population, the conditioned medium or the pharmaceutical composition of the invention with other active agents or treatment modalities, in the manner of the present invention for the amelioration of one or more symptoms associated with a disorder including, but not limited to, cancer, precancerous lesions, inflammatory diseases, autoimmune diseases, chronic pathologies, infectious diseases or an immunologically mediated disease including rejection of transplanted organs and tissues, and also, diseases associated to tissue loss and fertility disorders. These other agents or treatments may include known drugs and therapies for the treatment of such disorders. The cell, the cell population, the conditioned medium or the pharmaceutical composition of the invention may also be combined with corticosteroids, non-steroidal anti-inflammatory compounds, or other agents useful in treating cancer, inflammatory diseases, autoimmune diseases, chronic pathologies. The combined use of the agents of the present invention with these other therapies or treatment modalities may be concurrent, or given sequentially, that is, the two treatments may be divided up such that a cell population or a pharmaceutical composition comprising same of the present invention may be given prior to or after the other therapy or treatment modality. The attending physician may decide on the appropriate sequence of administering the cell population, or a pharmaceutical composition comprising same, in combination with other agents, therapy or treatment modality.

In another aspect, the present invention also relates to the cell, the cell population, the conditioned medium or the pharmaceutical composition of the invention for use in a cosmetic treatment.

In the present invention the term "cosmetic treatment" refers to the treatment to ameliorate the appearance of the skin, e. g. by improving the skin texture, in particular for the application to aged skin, in particular to crinkled, wrinkled and/or dimpled (cellulite) skin or to improve the appearance of burns. In this case, the cosmetic preparation is preferably formulated as cream, lotion, gel or wax, and may comprise a compound for improving the cosmetic effect. The cosmetic preparation is preferably applied cutaneously, subcutaneously or percutaneously, either topically, transdermally, intradermally or interepidermally. Advantageously the stem cell, the cell population, the conditioned medium or the pharmaceutical composition of the invention can be applied as easy as cosmetic filler, known from the state of the art. The stem cell preparation or conditioned medium may also be injected in several spots into the area, where the skin texture is to be ameliorated, e. g. around and/or under the crinkled, wrinkled and/or dimpled skin preferably 200 μL to 2 mL, most preferably 0.5 mL to 2 mL per spot.

In another aspect, the invention relates to an isolated stem cell, a cell population, a conditioned medium or a pharmaceutical composition of the invention for inhibiting or decreasing the proliferation and/or metastasis of tumor cells, the monocytic differentiation, the pathogenic microorganism growth and/or replication, or the peripheral blood mononuclear cells proliferation, or for enhancing or inducing the apoptosis of tumor cells, or for enhancing tissue regeneration (regenerative medicine), or for use in diagnostic, prognostic or treatment of fertility disorders or for use in the selection of germ cells.

The term "inhibiting" or "inhibition" of the proliferation and/or metastasis of tumor cells refers to stop, block or prevent, respectively, the cell division of a tumor cell, or to stop, block or prevent the spread of a tumor cell from one organ or part to another non-adjacent organ or part. Analogously, the term "decreasing" of the proliferation and/or metastasis of tumor cells refers, respectively, to reduce the cell division of a tumor cell, or to reduce the spread of a tumor cell from one organ or part to another non-adjacent organ or part.

The term "inhibiting" or "inhibition of the monocytic differentiation and/or peripheral blood mononuclear cells proliferation" refers to stop, block or prevent, respectively, the differentiation of monocytes into macrophages, or to stop, block or prevent the cell division of peripheral blood mononuclear cells. Analogously, the term "decreasing of the monocytic differentiation and/or peripheral blood mononuclear cells proliferation" refers, respectively, to reduce the differentiation of monocytes into macrophages, or to reduce the cell division of peripheral blood mononuclear cells.

The term "inhibiting" or "inhibition of the pathogenic microorganism growth and/or replication" refers to stop, block or prevent the cell division of the microorganism. As a consequence, the number of microorganisms decreases or remains constant.

The expression "enhancing the apoptosis of tumor cells" is similar to "inducing the apoptosis of tumor cells" and both means increasing or provoking the process of programmed cell death of tumor cells. Methods for measuring the inhibition or decrease of the proliferation and/or metastasis of tumor cells, the monocytic differentiation, the pathogenic microorganism growth and/or replication, or the peripheral blood mononuclear cells proliferation are shown in the examples of the present description, as well as methods for checking if the apoptosis of tumor cells is enhanced or induced. All these methods are widely known in the state of the art and are common practice for the skilled person.

On the other hand, the present invention also contemplates a kit comprising the cell, the cell population, the conditioned medium or the pharmaceutical composition of the invention, as well as the use of said kit for the treatment or prevention of cancer, inflammatory diseases, autoimmune diseases, chronic pathologies or infectious disease, diseases associated to tissue destruction or tissue loss, fertility disorders, and for inhibiting or decreasing the proliferation and/or metastasis of tumor cells, the monocytic differentiation or peripheral blood mononuclear cells proliferation, or for enhancing or inducing the apoptosis of tumor cells, or for enhancing or inducing tissue regeneration, or for use in diagnostic, prognostic or treatment of disorders. The invention also encompasses the use of the kit of the invention for cosmetic purposes.

Additionally, the corresponding methods of treatment equivalent to the uses of the cell, the cell population, the conditioned medium or the pharmaceutical composition of the invention disclosed herein, are also contemplated in the context of the present invention.

In this sense, in another aspect, the invention relates to a method for the treatment or prevention of cancer, inflammatory diseases, autoimmune diseases, chronic pathologies or infectious disease, diseases associated to tissue loss or fertility disorders, in a subject in need of treatment or prevention comprising administering to the subject a therapeutically effective amount of an isolated stem cell, a cell population, a conditioned medium, or the pharmaceutical composition of the invention.

Moreover the present invention refers to a method for inhibiting or decreasing the proliferation and/or metastasis of tumor cells, the monocytic differentiation or peripheral blood mononuclear cells proliferation, or for enhancing or inducing the apoptosis of tumor cells, or for enhancing or inducing tissue regeneration, or for enhancing the selection of germ cells or for use in diagnostic, prognostic or treatment of fertility disorders in a subject in need thereof comprising administering to the subject a therapeutically effective amount of an isolated stem cell, a cell population, a conditioned medium, or the pharmaceutical composition of the invention.

Unless otherwise defined, all technical and scientific terms used herein have the same meaning as commonly understood by one of ordinary skilled in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following examples, drawings and sequence listing are provided by way of illustration and are not intended to be limiting of the present invention.

The percentage of CD11 b expression for U937 cells treated with ASCs conditioned medium is 67%.

Figure 5:
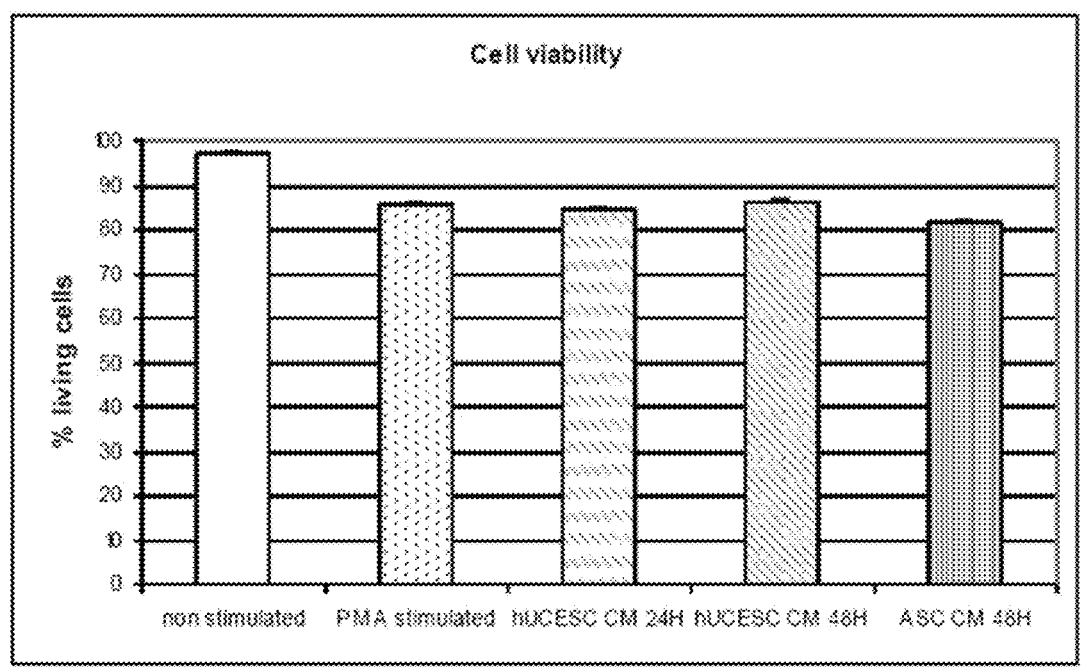
Figure 5:
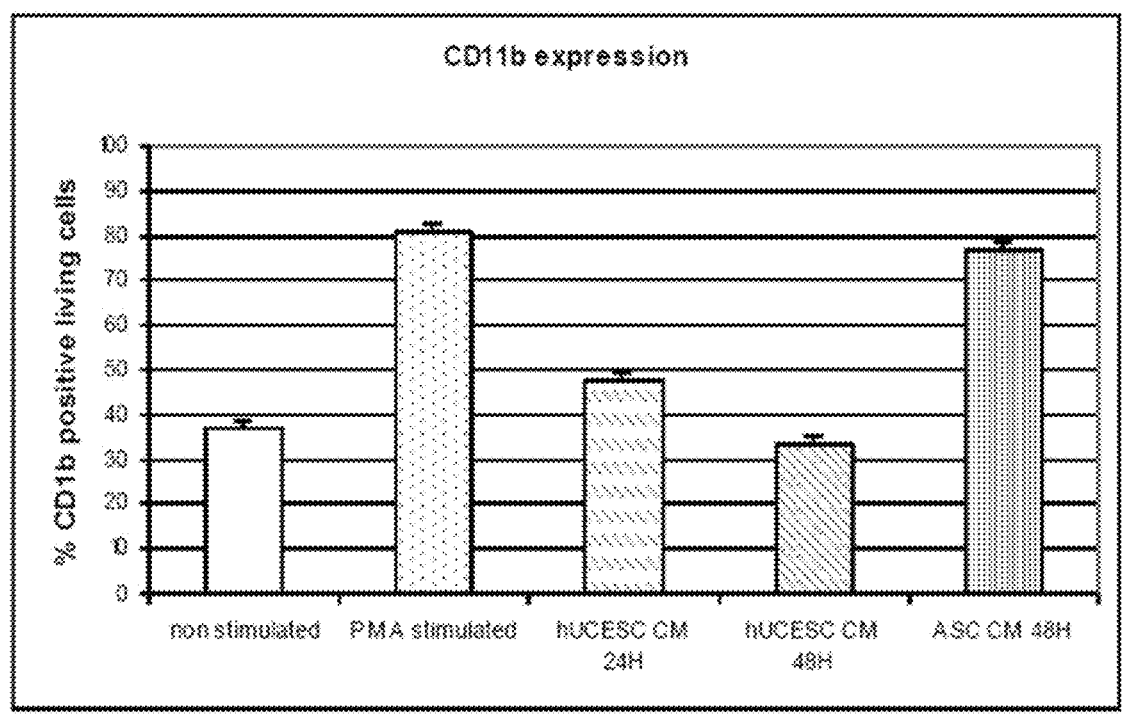

FIG. 5: Inhibition of monocytic differentiation: stimulation during 24 h and addition of hUCESCs conditioned medium. A) The viability of the U937 cells is higher than 80%. B) Basal level of U937 CD11b expression is 38%. Compared with the PMA treated control U937 cells, the percentage of cells stained positive for CD11b decreased from 82% in PMA treated U937 cells to 48% in U937 cell treated with hUCESCs conditioned medium produced during 24 hours (CM 24 hours) and to 34% in U937 cell treated with conditioned medium produced during 48 hours (CM 48 hours). Nevertheless the CD11 b expression in ASCs CM 48 hours treated U937 cells is 77%.

Figure 6:
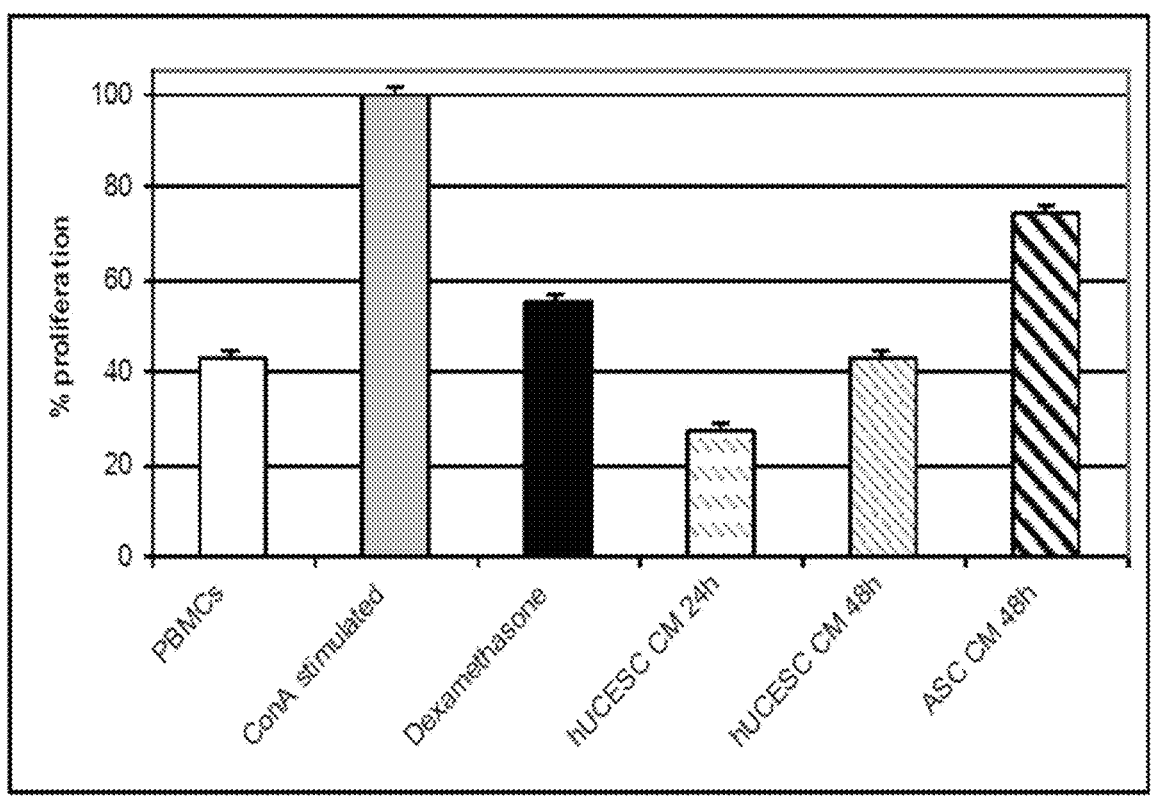

FIG. 6: Inhibition of PBMCs proliferation with conditioned medium. Both conditioned medium, 24 hours and 48 hours, suppressed PBMCs proliferation. The suppression is more effective with hUCESCs conditioned medium than ASCs conditioned medium. The magnitude of suppression by hUCESCs conditioned medium exceeded that of dexamethasone.

Figure 7:
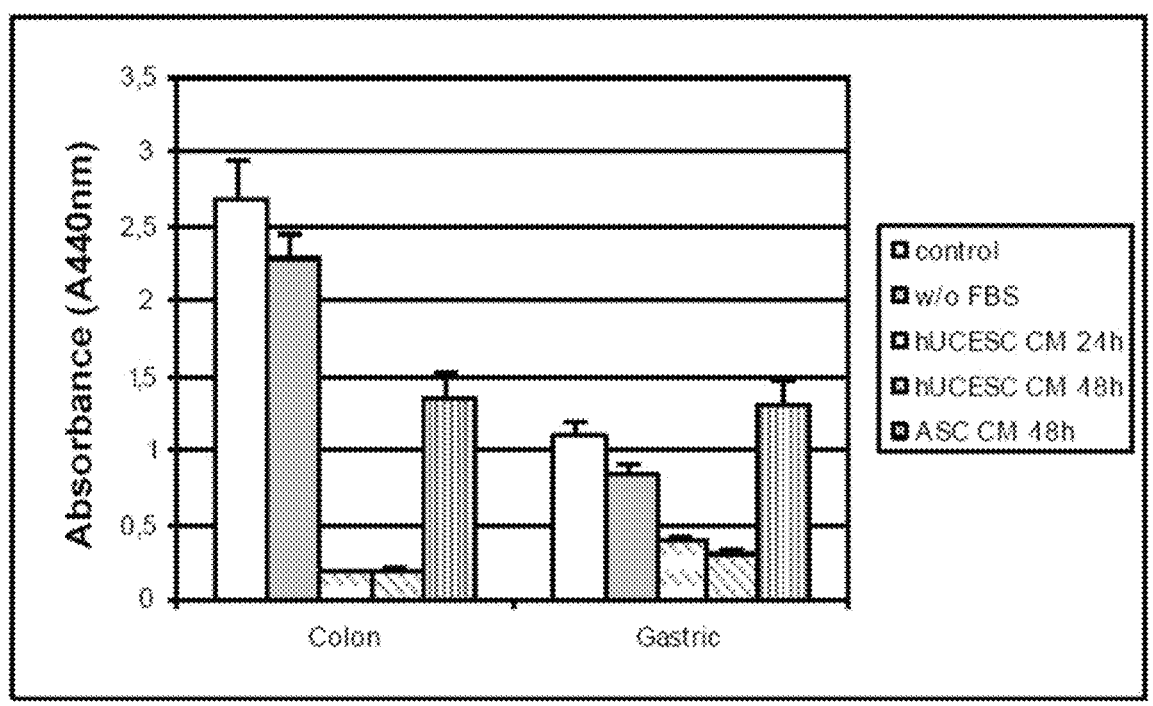
Figure 7:
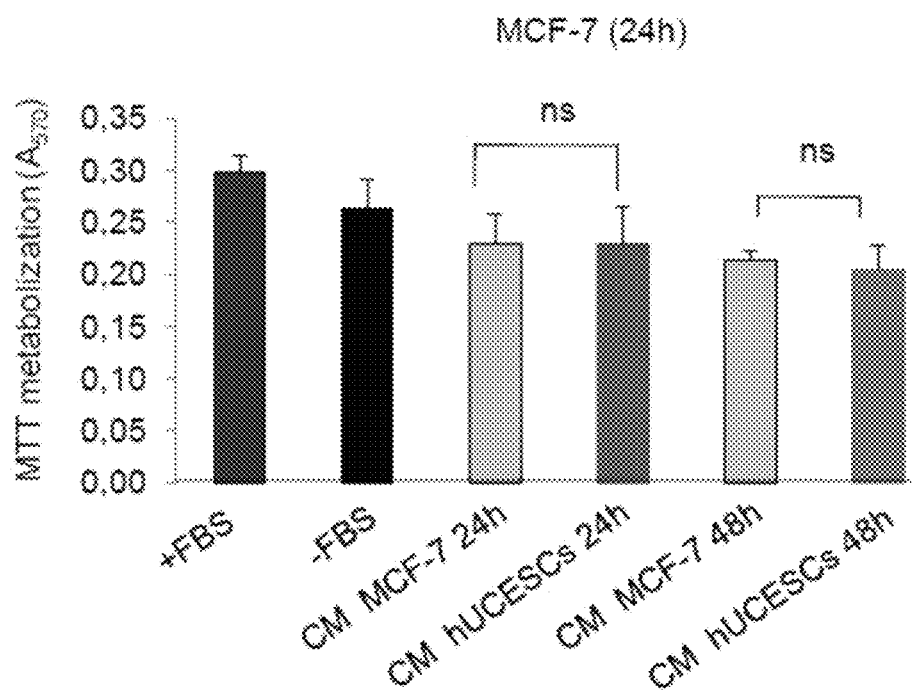
Figure 7:
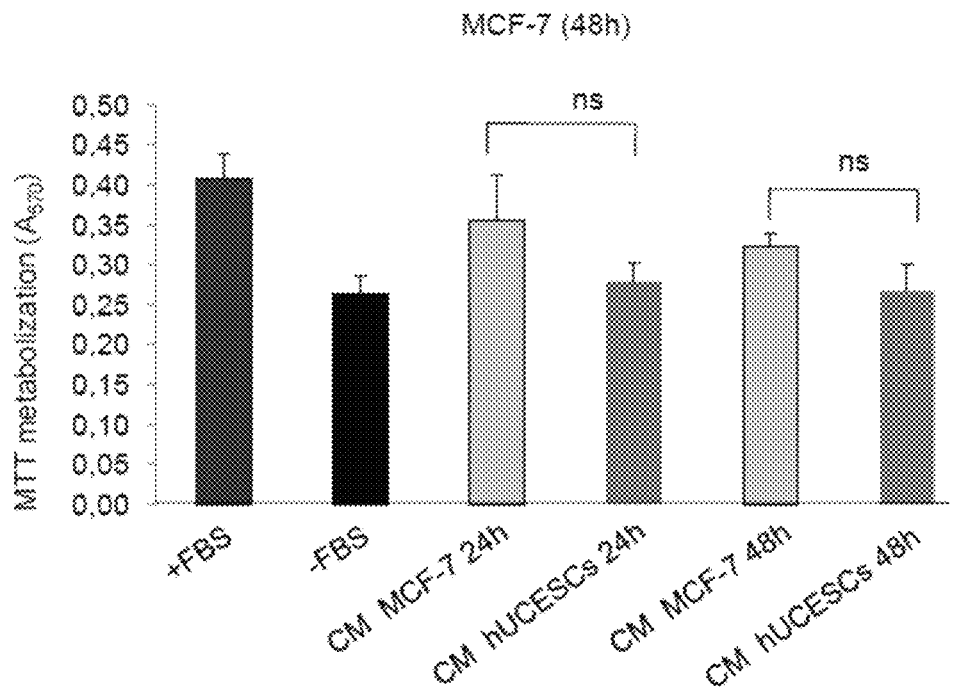
Figure 7:
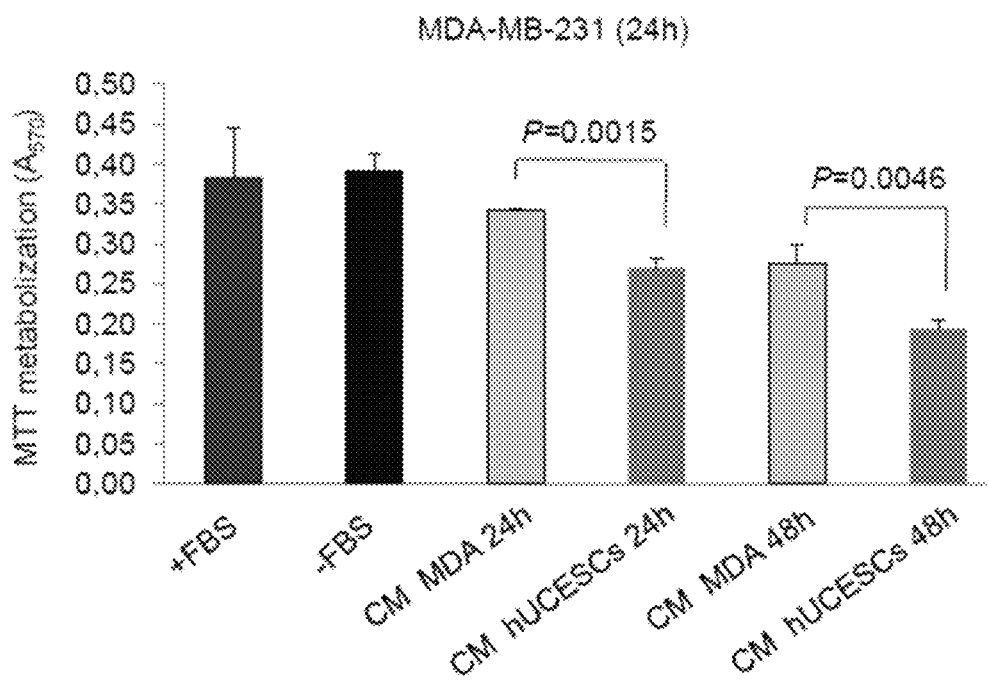
Figure 7:
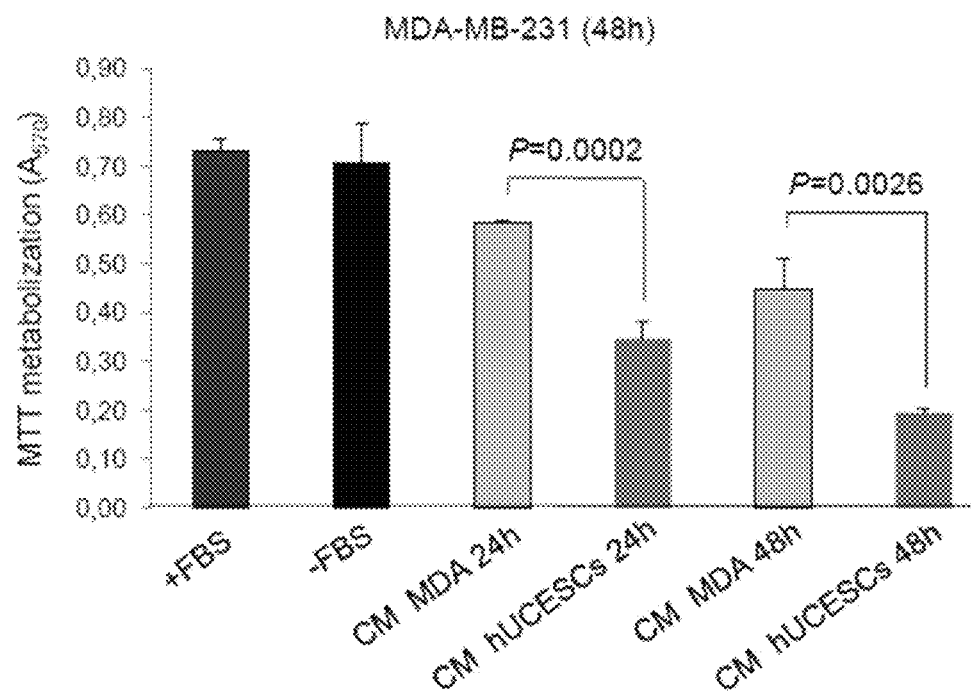
Figure 7:
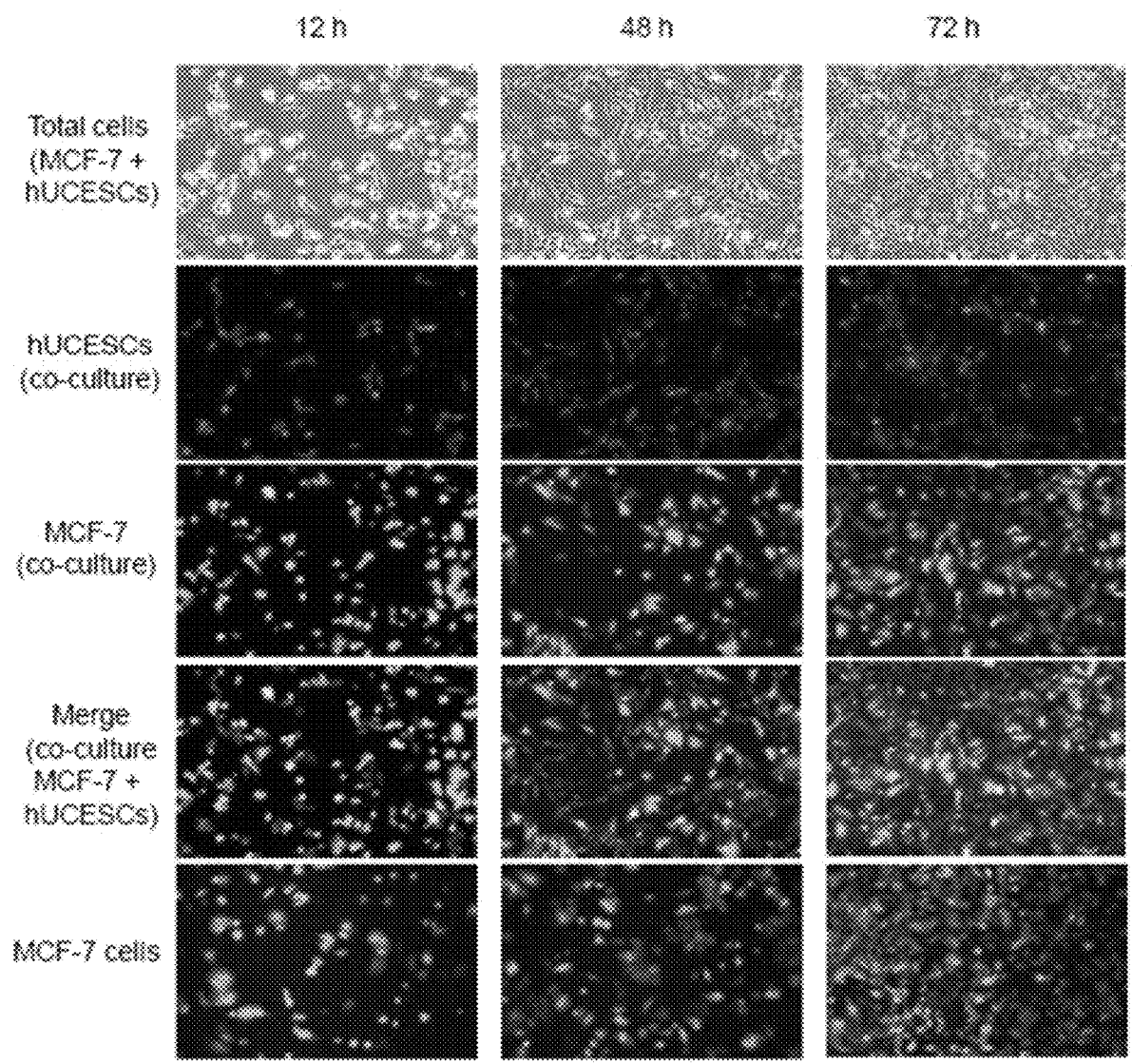
Figure 7:
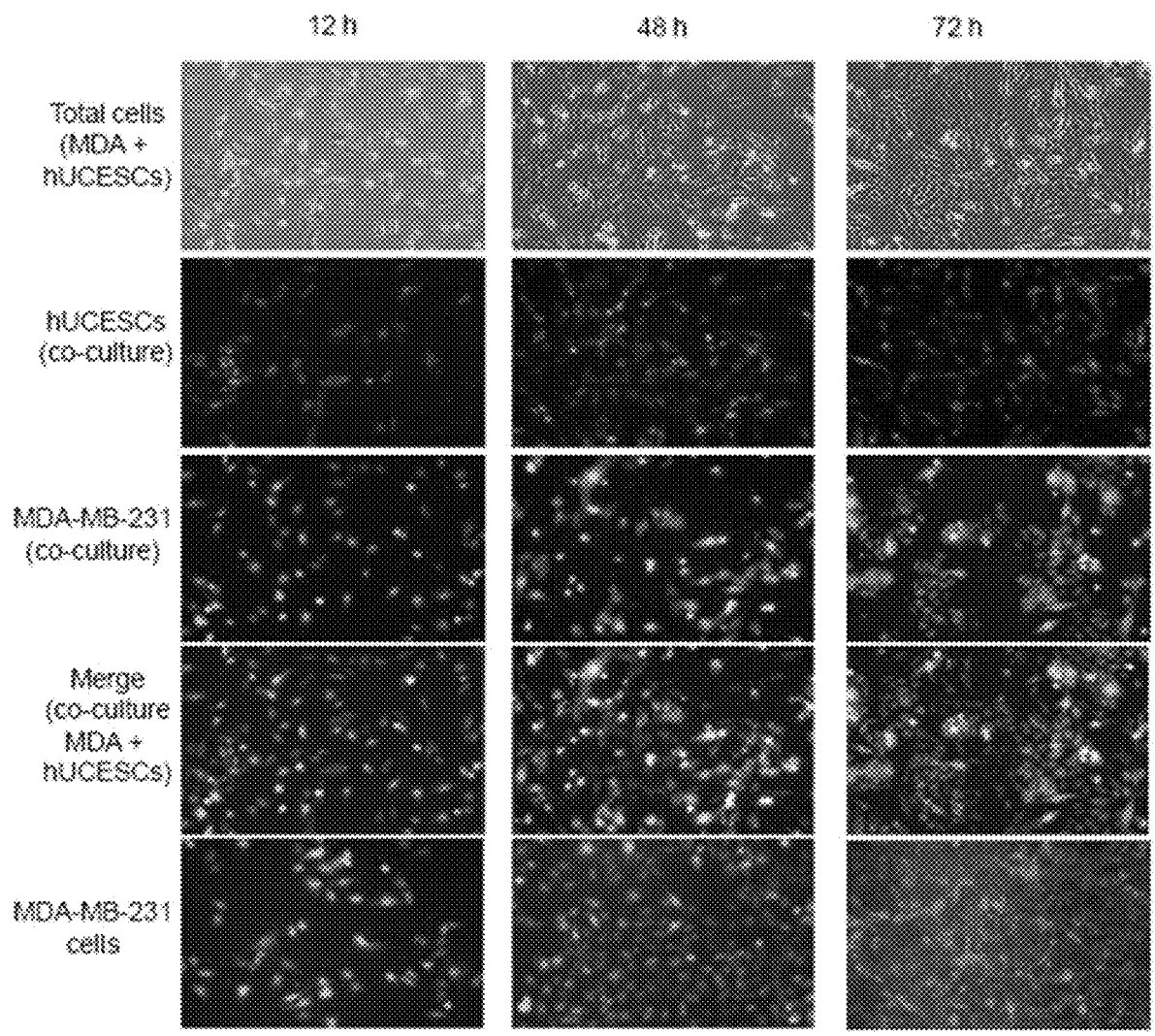

FIG. 7: Conditioned medium from hUCESCs reduces cell proliferation in HT29, AGS and MDA-MB-231 cells but not in the MCF-7 cell line. A. Cell proliferation assay of colorectal (HT29) and gastric (AGS) adenocarcinoma cell line treated during 48 hours with complete medium (control), incomplete medium (w/o FBS), conditioned medium from hUCESCs produced during 24 hours or 48 hours and conditioned medium from ASC produced during 48 h. B-C. MTT assay of MCF-7 cells treated during 24 or 48 hours with complete medium (+FBS), incomplete medium (−FBS), conditioned medium from MCF-7 cells produced during 24 or 48 hours, or conditioned medium from hUCESCs produced during 24 or 48 hours. D-E. MTT assay of MDA-MB-231 cells treated during 24 or 48 hours with complete medium (+FBS), incomplete medium (−FBS), conditioned medium from MDA-MB-231 cells produced during 24 or 48 hours, or conditioned medium from hUCESCs produced during 24 or 48 hours. F. MCF-7 cells ($1\times10^5$) were labeled with CellTracker Green dye and plated in 6-well plates. Four hours later, $1\times10^5$ hUCESCs labeled with CellTracker Red dye were added to MCF-7 cells and co-cultured in incomplete medium (without FBS) during 72 hours. Images were taken at 12, 48 and 72 hours. Last line show an example of MCF-7 cells growth in incomplete medium (−FBS), which was used as control of growth. G. MDA-MB-231 cells were labeled and co-cultured with hUCESCs as described in (F) for MCF-7 cells.

Figure 8:
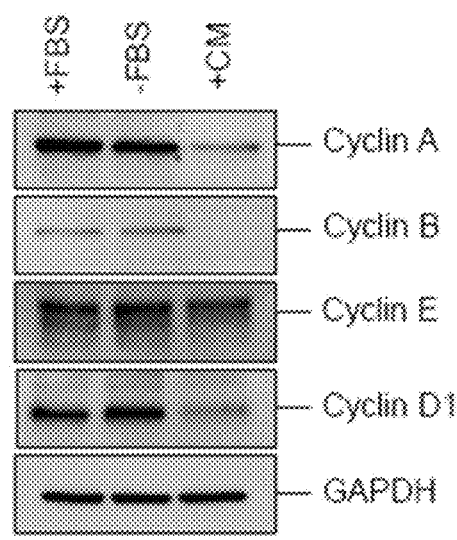
Figure 8:
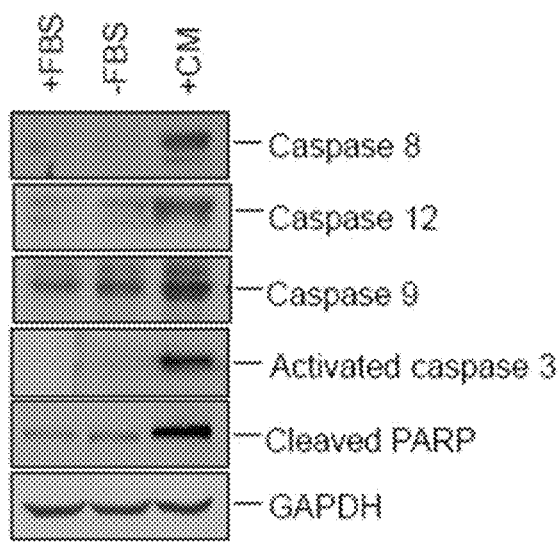
Figure 8:
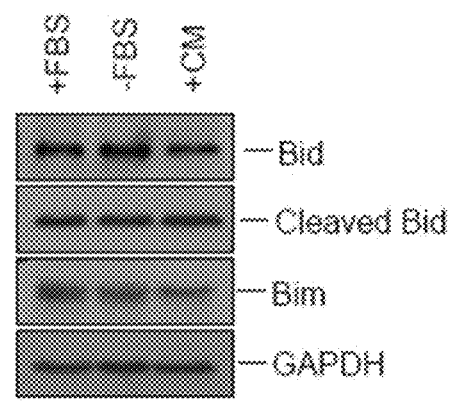

FIG. 8: Administration of conditioned medium (CM) from hUCESCs to MDA-MB-231 cells delay cell cycle and increase apoptosis. A. MDA-MB-231 cells were treated during 48 hours with DMEM plus 10% FBS (+FBS), incomplete medium (DMEM without FBS, −FBS), or CM of 48 hours from hUCESCs, and then subject to flow cytometry using propidium iodide (PI). Percentage of cells (mean±standard deviation) in each phase is showed. B. Western blot of cyclin A, cyclin B, cyclin E, cyclin D1, and GAPDH (used as loading control) of protein extracts from MDA-MB-231 cells treated during 48 hours as described in (A). C. Apoptosis was determined in MDA-MB-231 cells cultured during 48 hours with complete (+FBS), incomplete (−FBS), or CM from hUCESCs by flow cytometry using Annexin V/PI. Annexin V+/PI− and Annexin V+/PI+ indicates early and late apoptosis, respectively. D. Western blot of Caspase 8, -12, -9, activated caspase 3, and cleaved PARP of MDA-MB-231 protein extracts as indicated in (C). E. Western blots of the anti-apoptotic Bid, cleaved Bid, and Bim proteins in MDA-MB-231 extracts treated as in (C). GAPDH was used as loading control.

Figure 9:
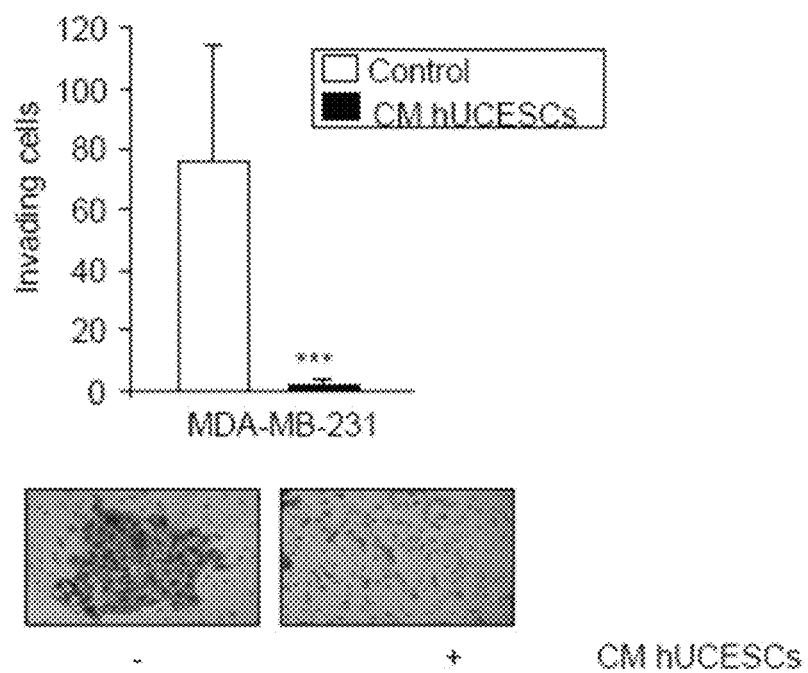
Figure 9:
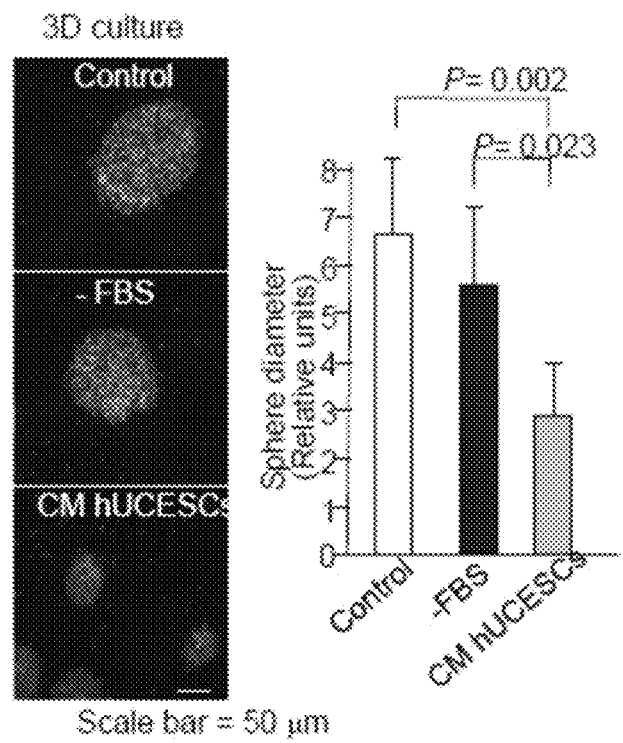
Figure 9:
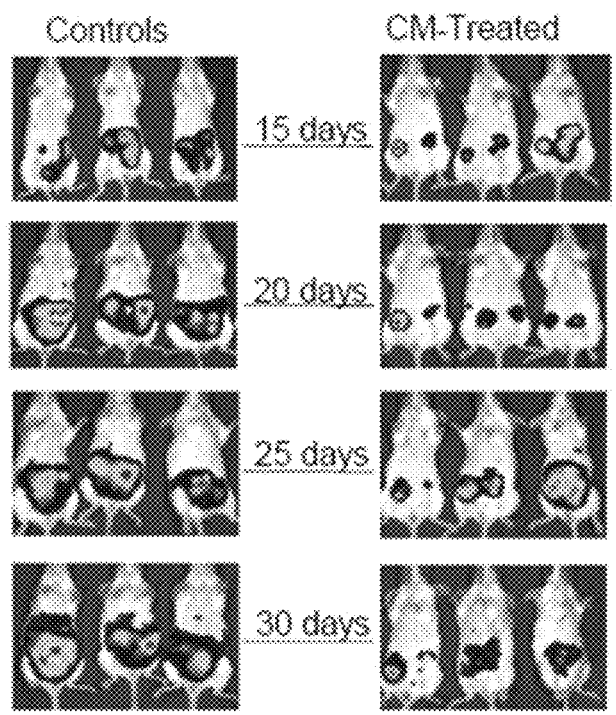
Figure 9:
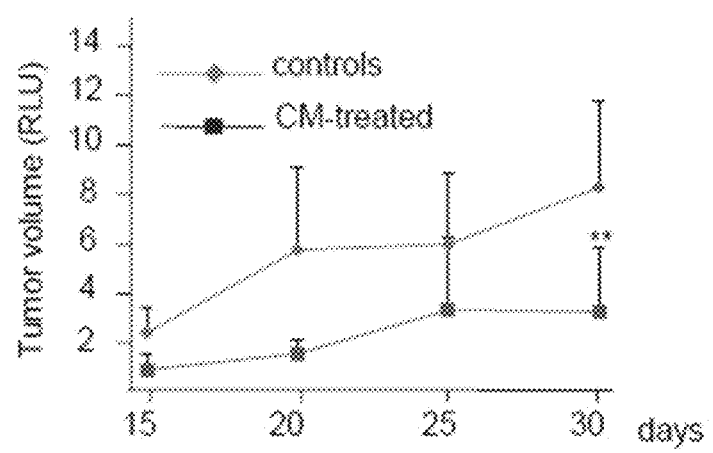
Figure 9:
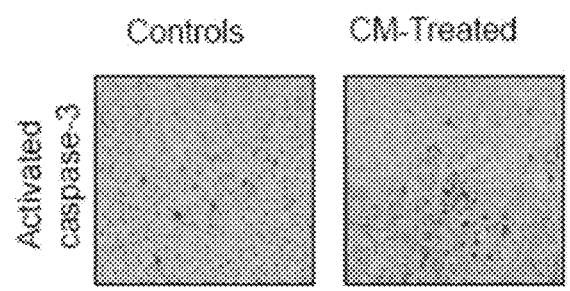
Figure 9:
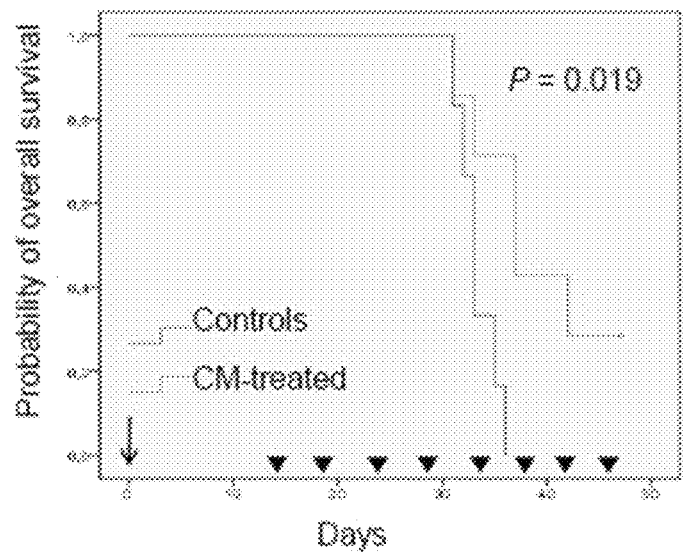

FIG. 9: Conditioned media (CM) from hUCESCs inhibits invasion, 3D growth, and tumour volume in a xenograft mice model. A. CM of 48 hours from hUCESCs significantly decreased MDA-MB-231 cells invasion through a matrigel matrix, as compared with cells with incomplete medium (−FBS, control). B. Administration of CM from 48 hours of hUCESCs culture during 9 days significantly reduces 3D growth of MDA-MB-231 cells, as compared with cells treated with complete (+FBS) or incomplete (−FBS) medium. C. Thirteen SCID mice were injected with MDA-MB-231-luc cells in the mammary fad pat. Fifteen days later, seven mice were intratumourally injected every five days with 150 µl of conditioned medium (CM) from hUCESCs (CM-treated) and six mice injected with incomplete medium (−FBS, controls). Representative images from controls and CM-treated mice were taken at 15, 20, 25, and 30 days. D. Tumour volume was determined by measuring luminescence. Values are expressed as mean±standard deviation of relative luminescence levels. **: P=0.011 vs. controls. E. Immunohistochemical detection of activated caspase-3 expression in representative tumours of SCID mice treated with CM and placebo, as described in (C). F. Kaplan-Meier plots of overall survival in CM-treated mice vs. control mice. Mice treated with CM had a long DFS compared with control mice. The difference was statistically significant (P=0.019).

Figure 10:
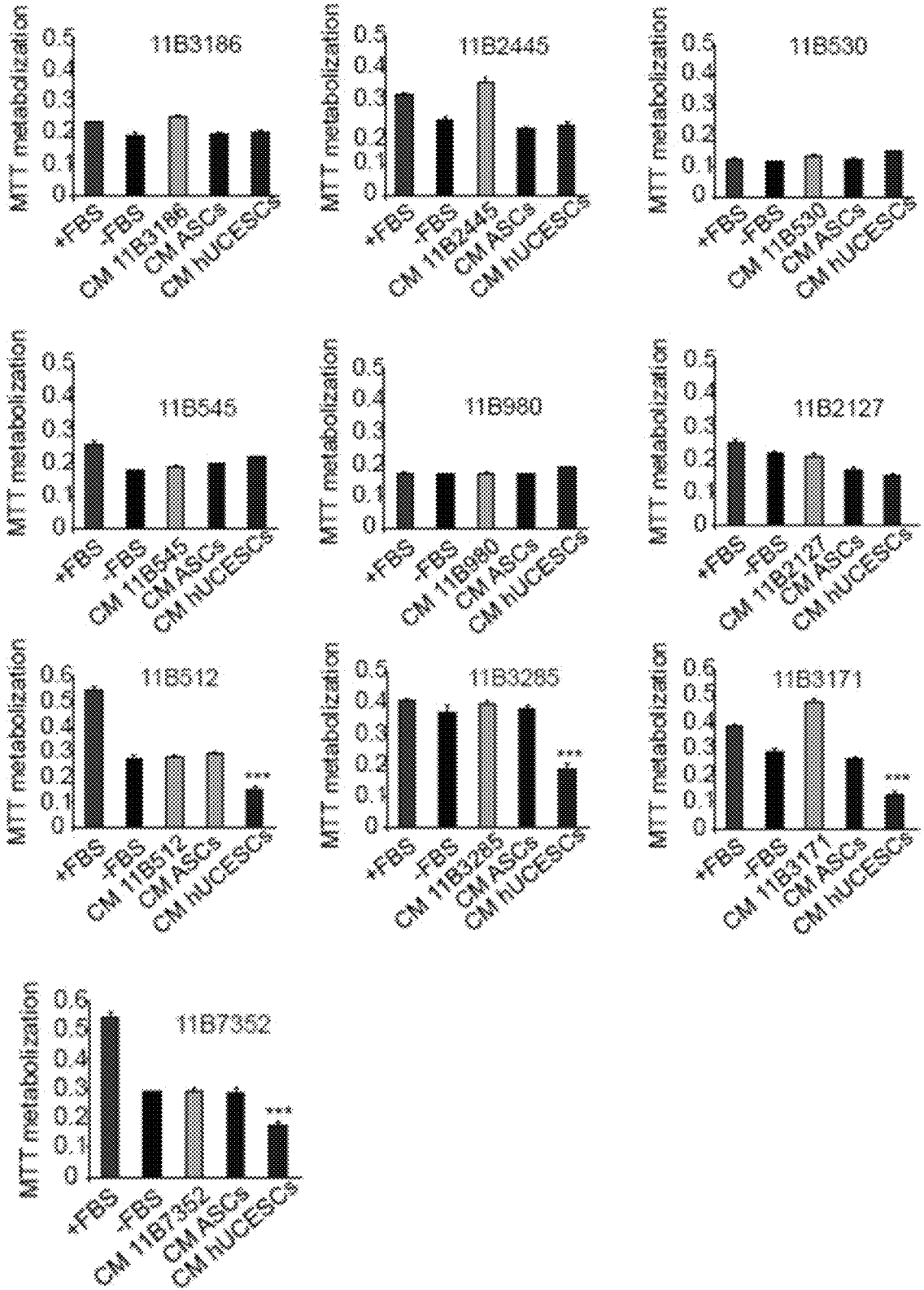
Figure 10:
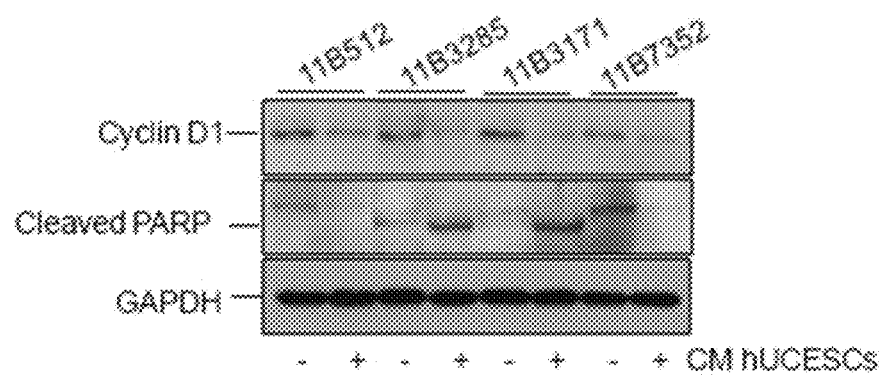

FIG. 10: Cell proliferation in primary cultures from breast tumours with high proliferating rate is significantly reduced after administration of conditioned media (CM) from hUCESCs. A. Ten primary cultures from human breast tumours were treated with: a) complete medium (+FBS), b) incomplete medium (−FBS), c) conditioned medium (CM) produced during 48 hours by the own cells, d) CM produced during 48 hours by adipose-derived stromal cells (ASCs), and e) CM produced during 48 hours by hUCESCs. After 48 hours of culture, an MTT assay was carried out to evaluate cell proliferation. Cultures with high proliferation rate (11B512, 11B3285, 11B3171, and 11B7352, in red) showed a significant (***: P<0.001) decrease in proliferation after treatment with CM from hUCESCs, as compared with others treatments. B. Protein extracts from primary cultures with high proliferation rate treated with CM from hUCESCs or with incomplete medium (−FBS) were incubated with cyclin D1, cleaved PARP, and GAPDH (used as loading control) antibodies and assayed for Western blot.

Figure 11:
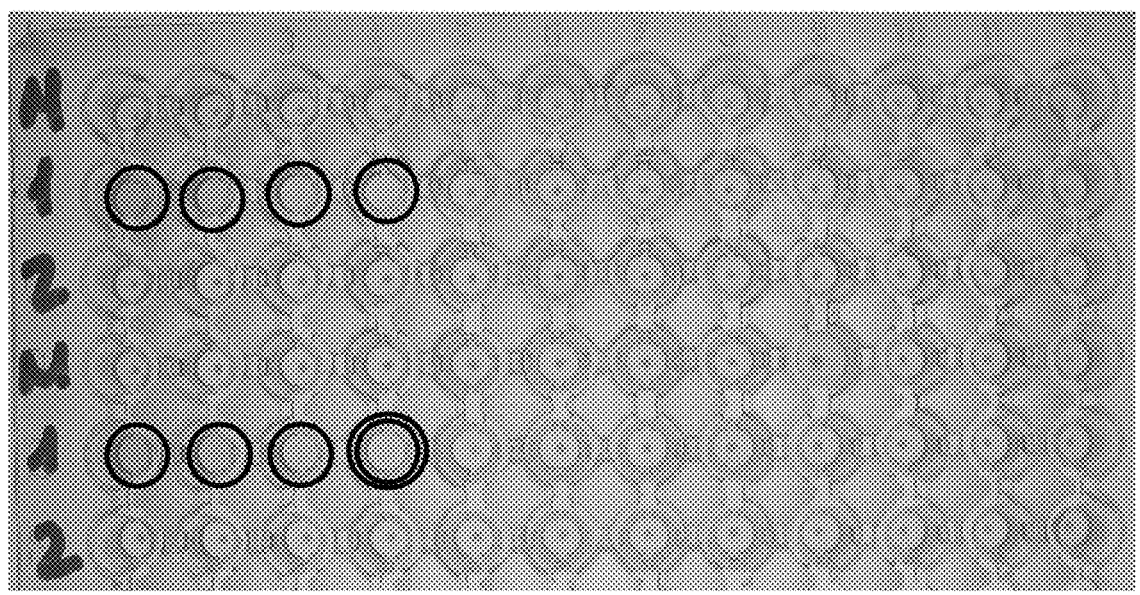

FIG. 11: Representative example of growth inhibition of pathogenic microorganism by hUCESCs conditioned medium in 96 microwell plates. A. Control media (M) showed *E. Coli* growth, and hUCESCs conditioned medium (1) showed an inhibition of bacterial growth up to well 4 (1/20 dilution). Adipose tissue-derived MSC conditioned medium bacterial growth in all wells. B. Table of volumes added in wells for each condition. Circles indicate wells showing bacterial growth inhibition.

Figure 12:
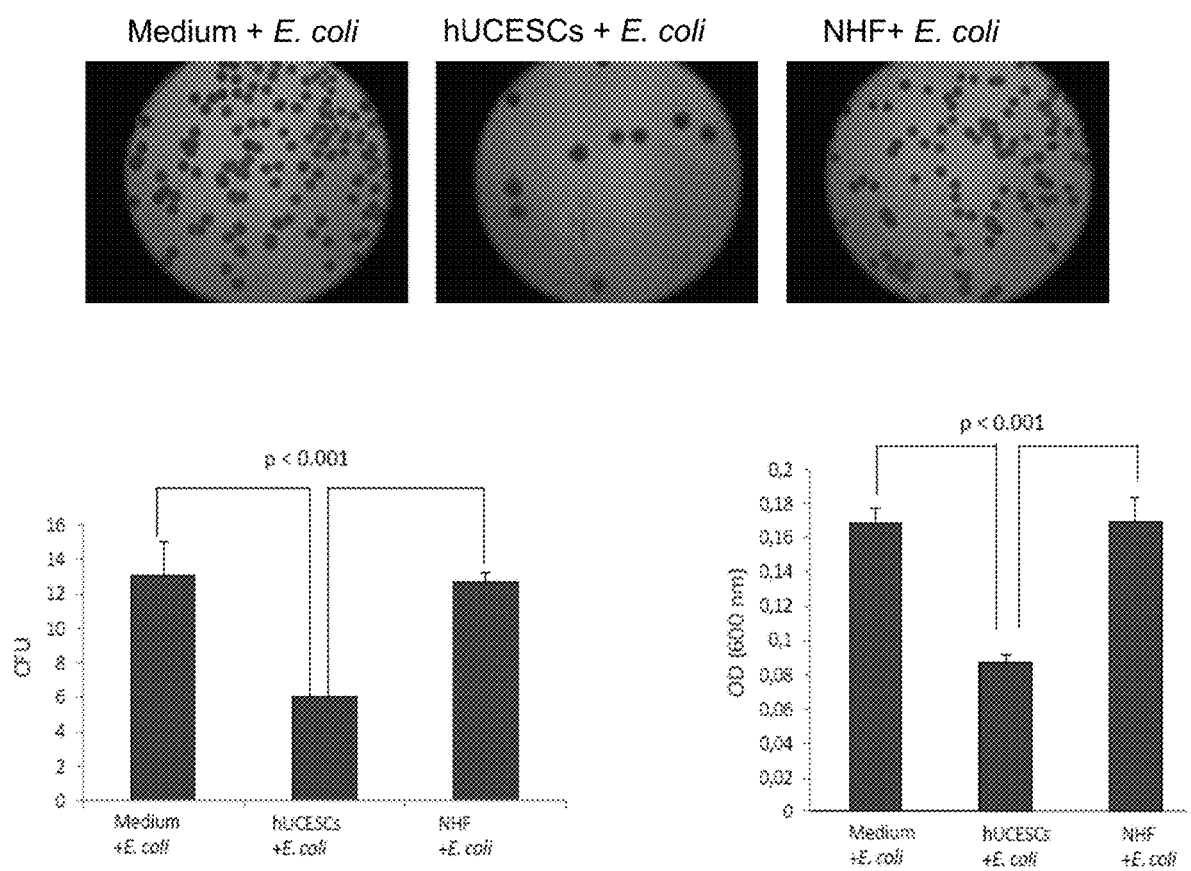

FIG. 12: Representative example of growth inhibition of microorganism by hUCESCs. Significative (p<0.001) inhibition of microorganism growth by hUCEScs, analyzed by CFU counting and OD. Medium alone and normal human fibroblast (NHF) show no inhibition of *E. Coli* growth.

Figure 13:
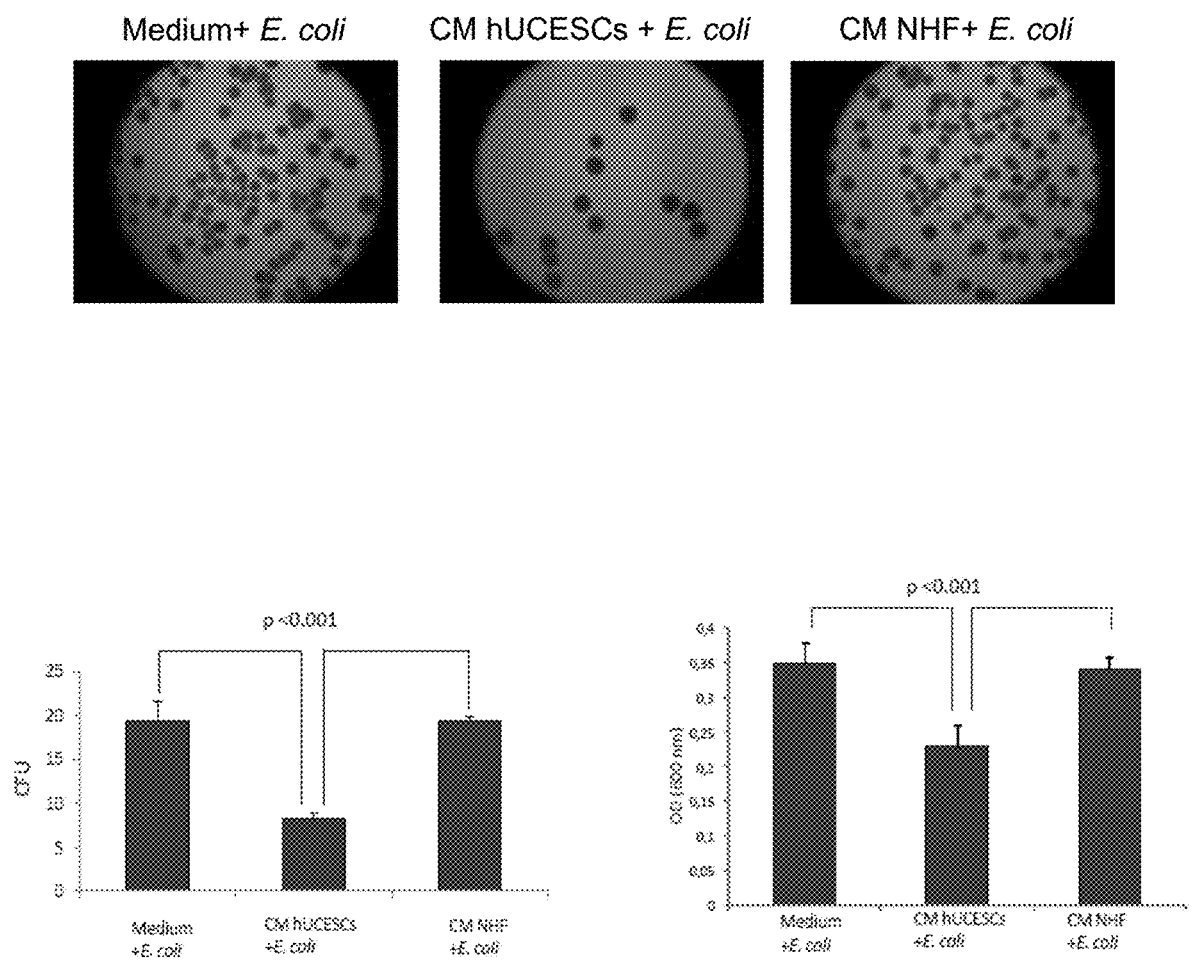

FIG. 13: Representative example of growth inhibition of microorganism by hUCESCs conditioned medium. Significative (p<0.001) inhibition of microorganism growth by hUCEScs conditioned medium (CM), analyzed by CFU counting and OD. Medium alone and normal human fibroblast conditioned medium (CM NHF) show no inhibition of *E. Coli* growth.

Figure 14:
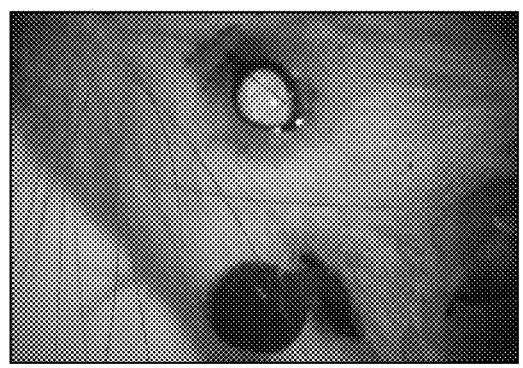
Figure 14:
Figure 14:
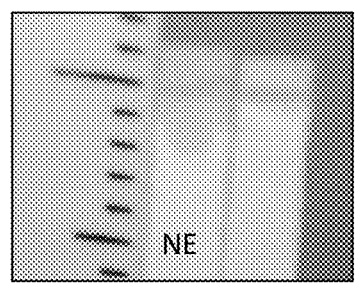

FIG. 14: Model of dry eye in rat. A. Photograph showing the extraorbital lacrimal gland before excision. B. An Adapted schirmer test was used to measure tear production. C. Schirmer's Test showing results in normal eye (NE) and dry eye (DE) 7 days after extraorbital lacrimal gland excision in the dry eye.

Figure 15:
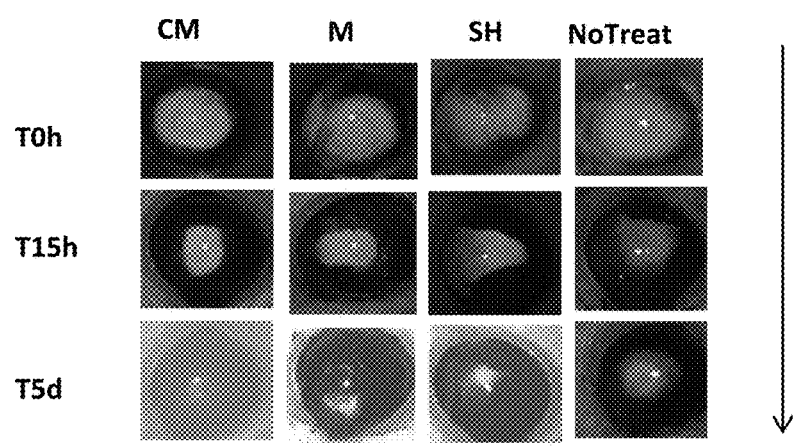
Figure 15:
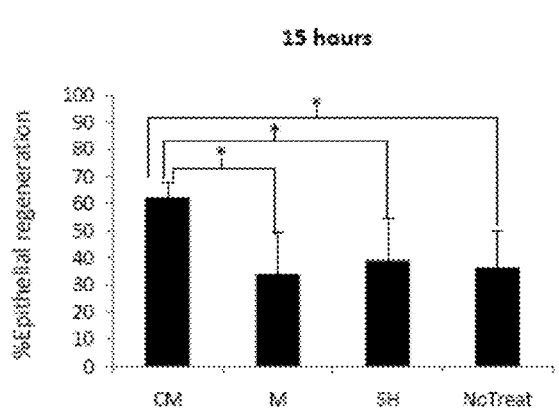
Figure 15:
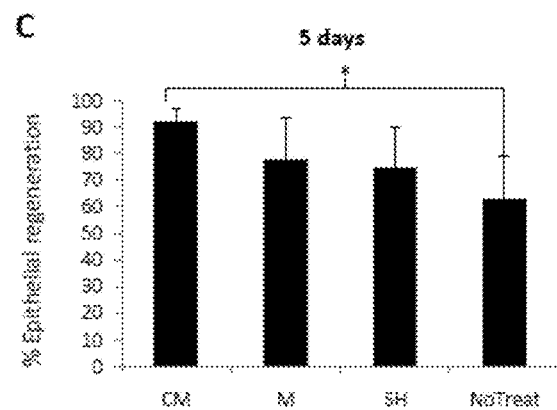

FIG. 15: 'In vivo' epithelial regeneration. A. Representative images of fluorescein staining of the cornea just after the alkali burn (T0h), 15 hours after (T15 h) and 5 days after (T5 d). B. Statistical analysis of the percent of epithelial corneal regeneration 15 hours after the alkali burn (*p<0.005). C. Statistical analysis of the percent of epithelial corneal regeneration 5 days after the alkali burn (*p=0.005). Treatments used were the conditioned medium (CM), Medium alone, without any previous contact with cells (M), Oftalmic drops with sodium hyaluronate (SH) and no treatment (NoTreat).

Figure 16:
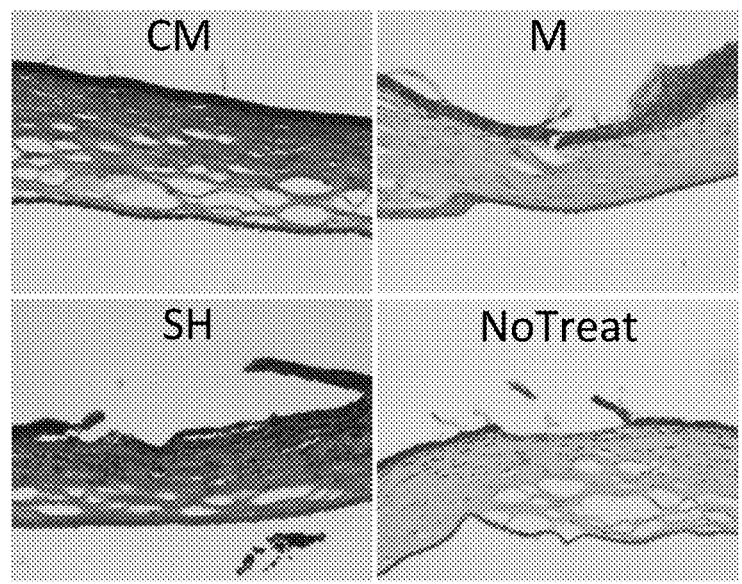

FIG. 16: Histology. Representative images of hematoxylin eosin staining of 20p slides from corneas treated with conditioned medium (CM), Medium alone, without any previous contact with cells (M), Oftalmic drops with sodium hyaluronate (SH) and no treatment (NoTreat) 5 days after the alkali burn (Magnification, ×10).

Figure 17:
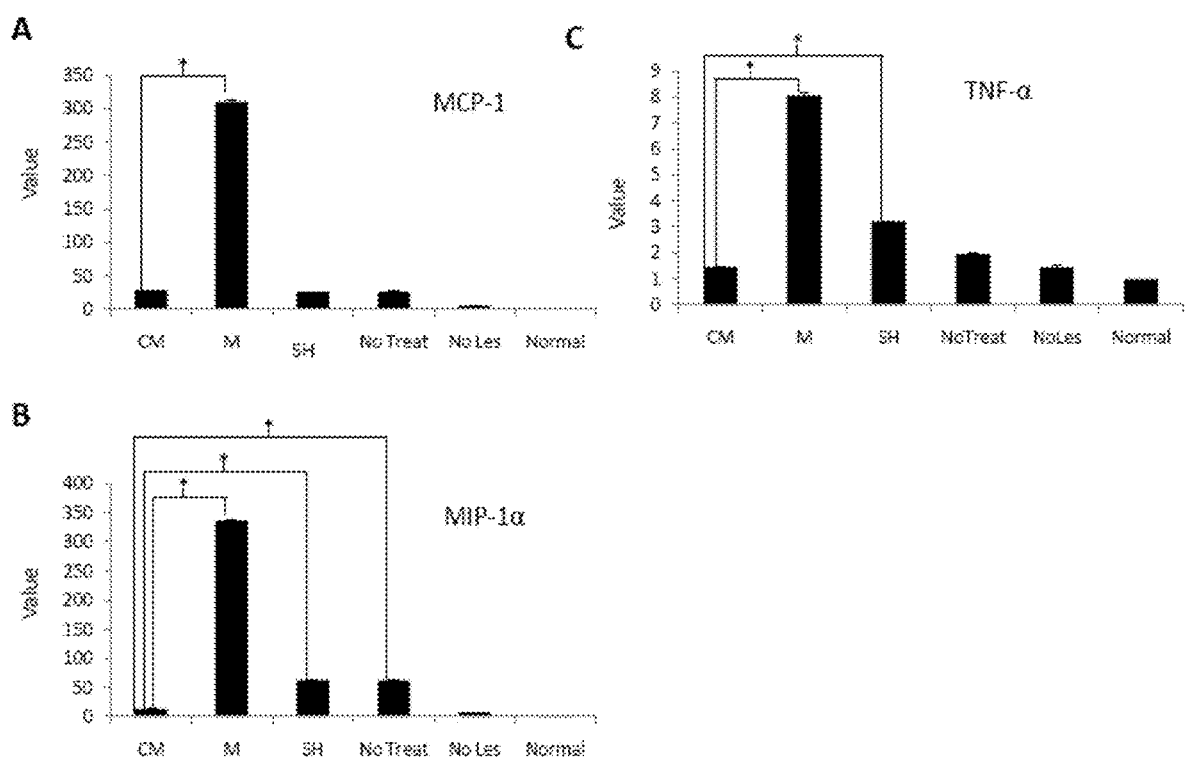

FIG. 17: Anti-inflammatory effects. A-C. Statistical analysis of real-time PCR results of MCP-1 (A), MIP-1α (B) and TNF-α (C) of corneas 5 days after the alkali burn. Conditions analyzed were corneas treated with conditioned medium (CM); corneas treated with medium alone without any previous contact with cells (M); corneas treated with Oftalmic drops with sodium hyaluronate (SH), corneas from dry eyes but without any lesion (NoUlc) and corneas from healthy eyes without any lesion (Normal).

Figure 18:
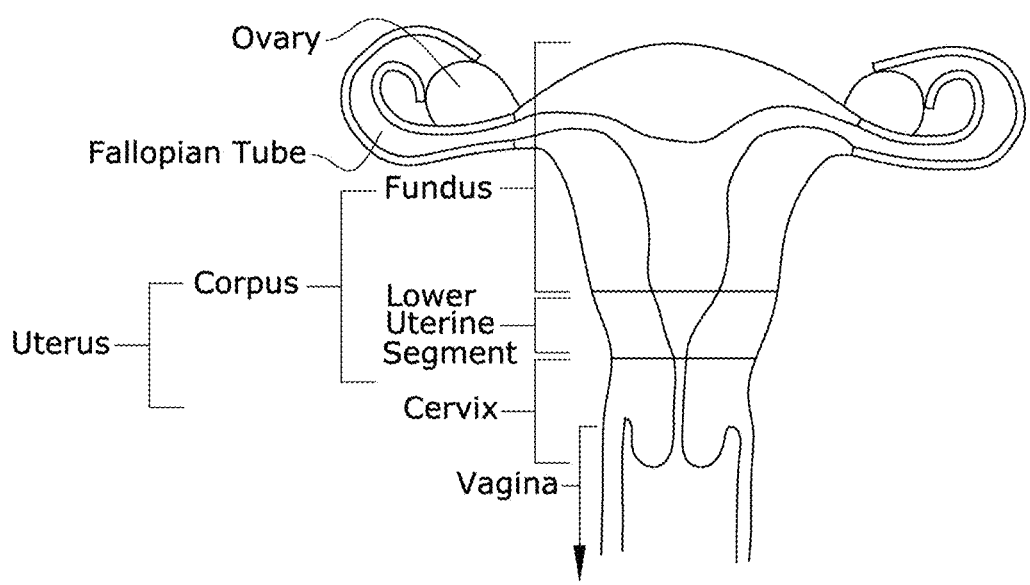
Figure 19:
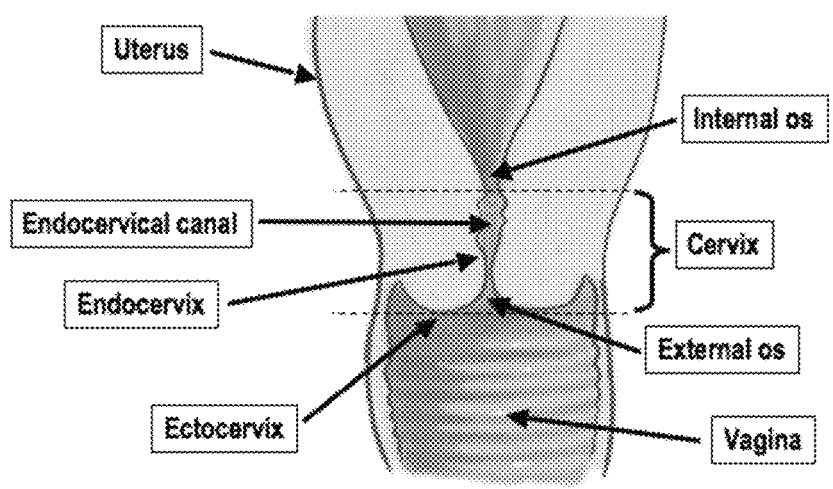

FIG. 18 and FIG. 19 are schematic figures of the female reproductive system.

EXAMPLES

Example 1: Isolation and Characterization of Human Uterine Cervical Stem Cells

I—Material and Methods

Isolation and Growth of Human Uterine Cervical Stem Cells

Human uterine cervical stem cells (hUCESCs) were obtained from an exfoliation of the uterine cervix during routine gynaecological examination. Briefly, cytological sample was enzymatically disaggregated with trypsin, collagenase or other enzyme which can disaggregate the cervical mucus. Then, the sample was centrifuged 5 minutes at 400 g and the pellet was collected and seeded in a culture plate. The well can be previously coated with 1% gelatin or fibronectin or other substrate to allow the adherence. Sample was culture in Dulbecco's Modified Eagle Medium: Nutrient Mixture F-12 (DMEM-F12), glutamine, with or without antibiotics, with serum, epidermal growth factor (EGF), hydrocortisone, insulin, non-essential amino acids, sodium pyruvate. The subculture of cells was carried out with trypsin or accutase or other proteolytic and/or collagenolytic enzymes.

Flow Cytometry Characterization

Human uterine cervical stem cells (hUCESCs) were stained with a panel of specific monoclonal antibodies: CD29-PE, CD45-FITC, CD90-PE, CD105-PE, HLA-DR-PE (Beckman Coulter), CD44-PE, CD73-PE, CD31-PE, TRA1-81-FITC (Becton Dickinson, Biosciences Pharmingen), CD34-FITC, CD117-PE and CD133-PE (Miltenyi Biotec). 7-amino-actinomycin-D (7-AAD) (BD Pharmingen) was added for dead cell discrimination. Immunophenotyping was performed on the same cells aliquoted equally into different tubes. Stained cells were re-suspended in PBS and analysed using Cytomics FC500 flow cytometer (Beckman Coulter). The computed data were analysed using CXP software provided by the manufacturer.

Immunocytochemistry Characterization

Human uterine cervical stem cells (hUCESCs) were cultured as above described. $3 \times 10^4$ cells were seeded in slides, and fixed for 10 minutes in 96% ethanol, before processing for immunocytochemistry. Mouse tumours were immersion-fixed in 10% neutral buffered formalin for 24 hours and embedded in paraffin routinely.

Sections 4 μm thick were mounted on Flex IHC microscope slides (Dako, Glostrup, Denmark). The immunohistochemical (IHC) techniques were automatically performed in an AutostainerLink 48 (Dako). FLEX ready-to-use Dako primary antibodies to CK (clone AE1/AE3), E-cadherin (clone NCH-38), vimentin (clone V9), desmin (clone D33), actin (clone HHF35), smooth muscle actin (clone 1A4), and β-catenin (clone beta-catenin-1) were employed. A ready to use monoclonal antibody to p63 (clone 4A4) from Abcam (Cambridge, UK) was also used. KLF4, OCT4, and Sox2 primary antibodies were obtained from Santa Cruz Biotechnology, Millipore, and Sigma-Aldrich, respectively. Epitope retrieval was performed in a microwave 20 minutes using EnVision FLEX target retrieval solution (pH 9). All antibodies were incubated for 20 minutes at RT except p63 which was incubated for 30 minutes. As detection system we used EnVision FLEX/HRP Dako (dextran polymer conjugated with horseradish peroxidase and affinity-isolated goat anti-mouse and anti-rabbit immunoglobulins) for 20 minutes. For E-cadherin a mouse linker (Dako) was added.

Growth Rate

The rate of proliferation of hUCESCs was determined by counting the total number of cells in duplicate wells every day for 12 days. Initially, cells were seeded at 2,000 cells/well in a 6-well plate culture.

Spheroid Formation and Adipose Differentiation hUCESCs were cultured in DMEM/F12 medium (vol/vol) (Invitrogen), 1% B27 (Invitrogen), 10 ng/mL epidermal growth factor (EGF) and 5 ng/mL fibroblast growth factor 2 (FGF-2), 100 IU/mL penicillin, and 100 µg/mL streptomycin in a 60 mm dish, and 5-7 days after spheroids were photographed. To induce adipose differentiation hUCESCs were cultured in hMSC Differentiation Bulletkit-Adipogenic medium (Lonza Biologics, Walkersville, USA) in 60 mm dish during 12 days, and then formaldehyde fixed for Oil Red O staining (Sigma).

Conditioned Medium Production

Cells were plated at a density of $3 \times 10^4$ cells/cm$^2$ in DMEM:F12 medium with 10% FBS and antibiotics. After 48 hours, the cells were washed three times with phosphate buffered saline (PBS) and then, cultured in DMEM:F12 without FBS for 24 hours or 48 hours. Then, the medium was collected as conditioned medium (CM), centrifuged 10 minutes at 300 g and used immediately or kept at $-20°$ C.

II—Results

Figure 1:
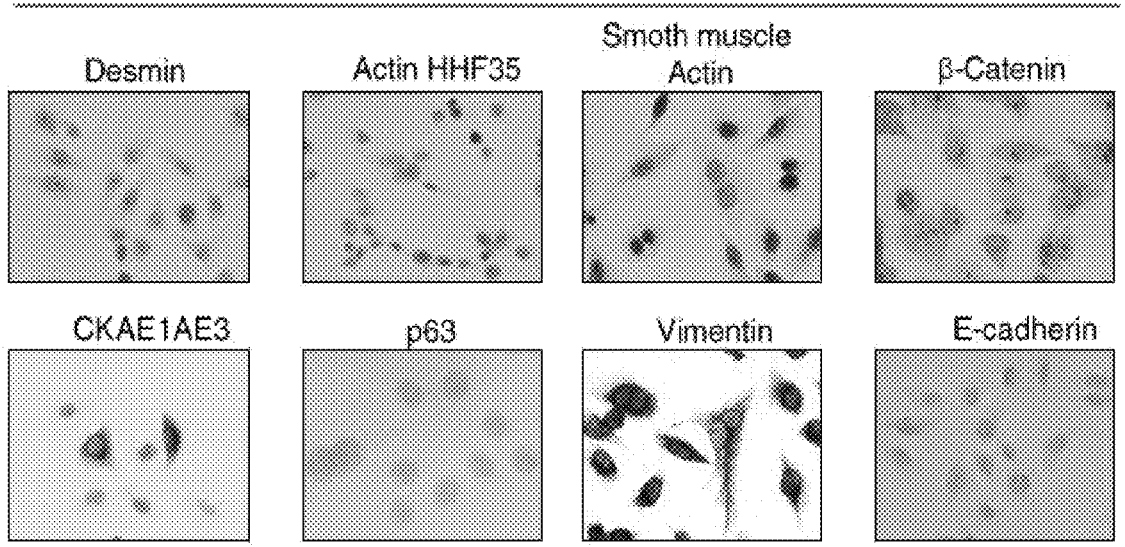
FIG. 1: Uterine cervical stem cells show immune phenotype of adult mesenchymal stem cells. A. Cells obtained from cervical smear and cultured during 90 days were immunolabeled with specific antibodies and then evaluated for protein expression. Desmin, actin HHF35, smooth muscle actin, p63, and E-cadherin expression was not detected, while CKAE1AE3 was focally expressed, and vimentin show strong expression. B. Specific stem cell markers such as klf4, oct4, and sox2 showed strong immunolabeling in uterine cervical stem cells. C. Flow cytometry analyses of human uterine cervical stem cells (hUCESCs) indicate high percentage of CD29, CD44, CD73, CD90 and CD105 proteins, but negative expression of CD31, CD34, CD45, CD117, CD133, HLA-DR, and Tra1-81 proteins. D. Isolated hUCESCs form spheroids when are cultured in specific medium.
Figure 1:
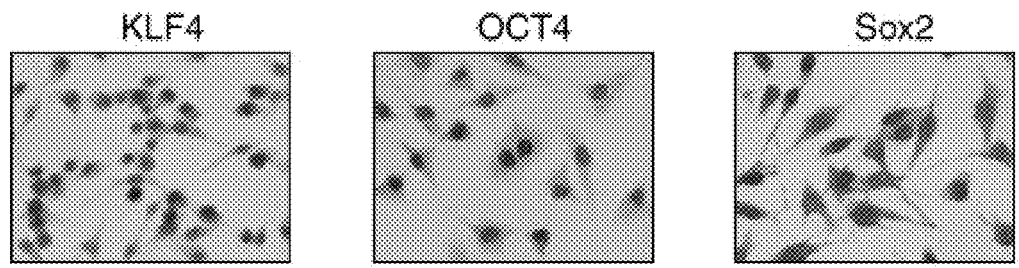
Figure 1:
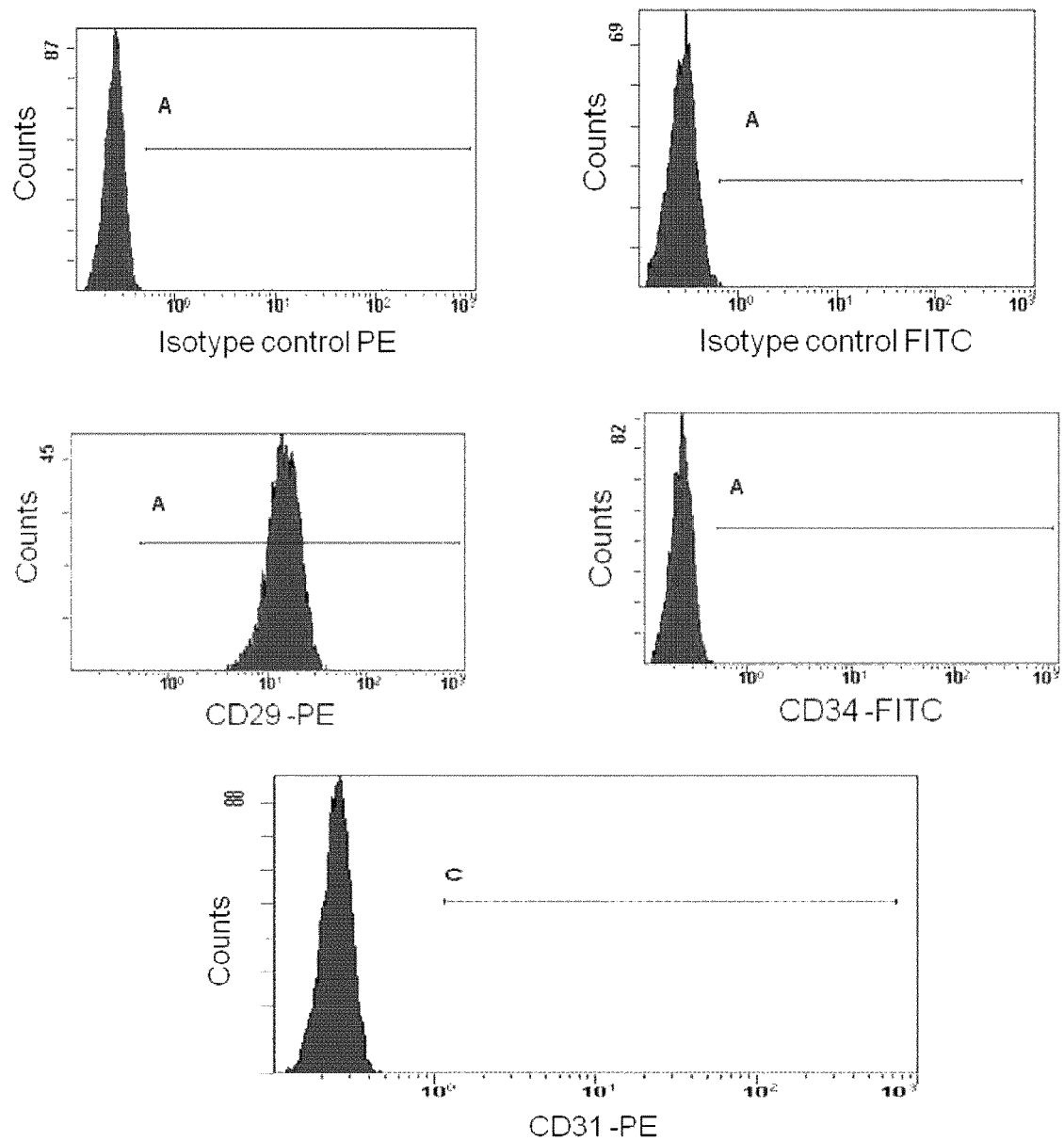
Figure 1:
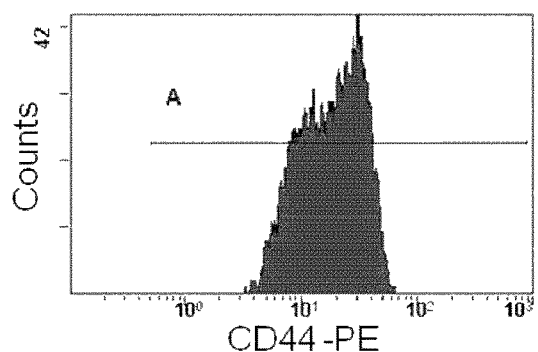
Figure 1:
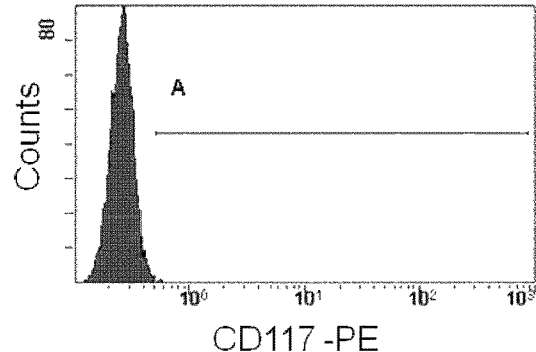
Figure 1:
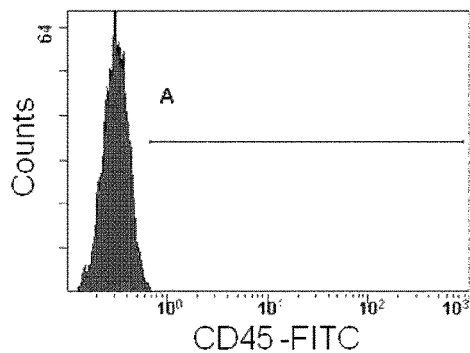
Figure 1:
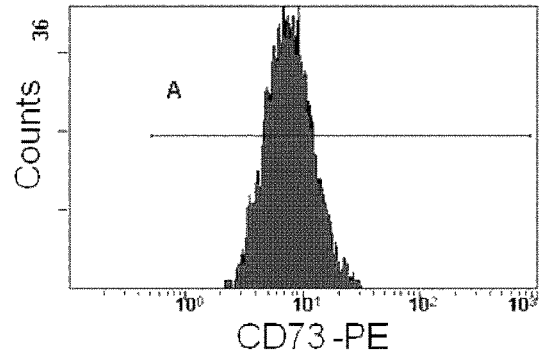
Figure 1:
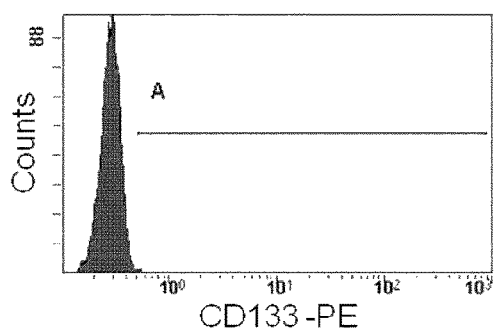
Figure 1:
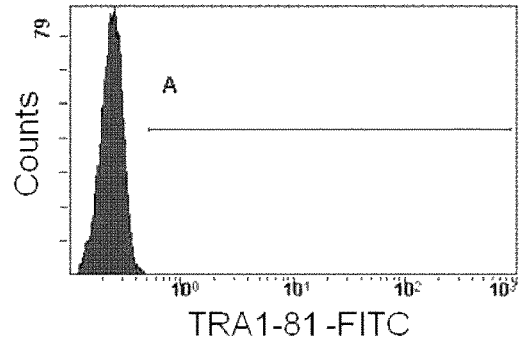
Figure 1:
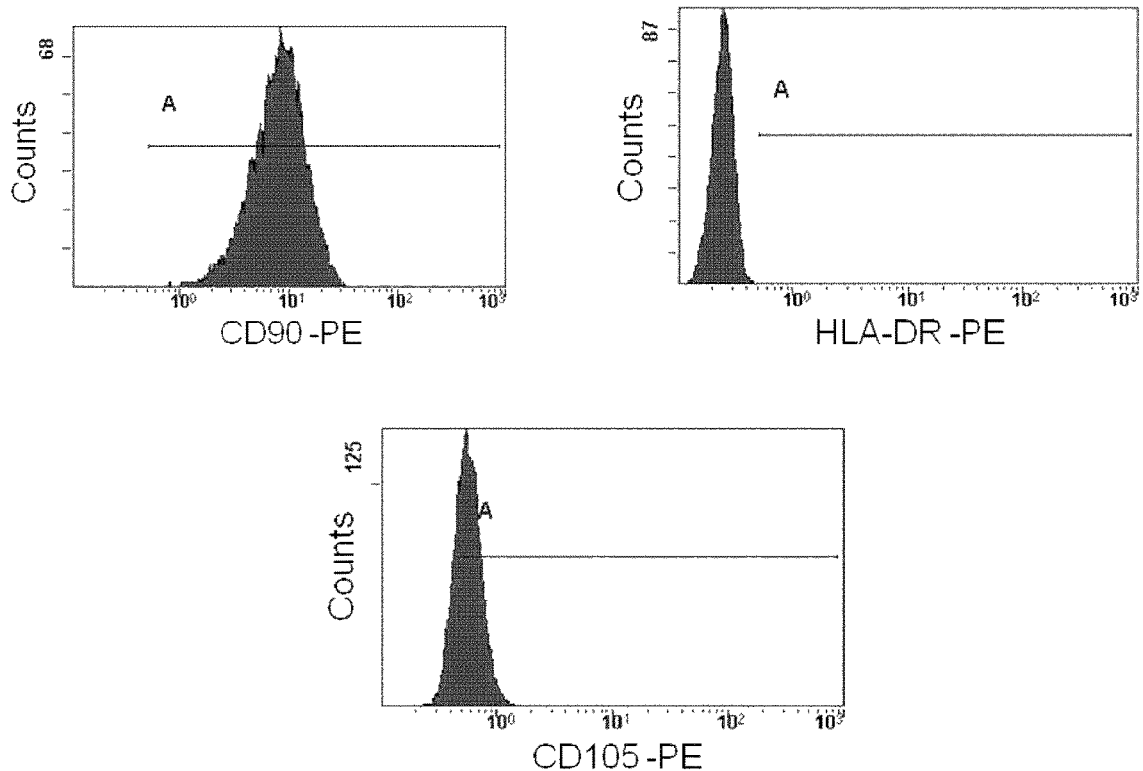
Figure 1:
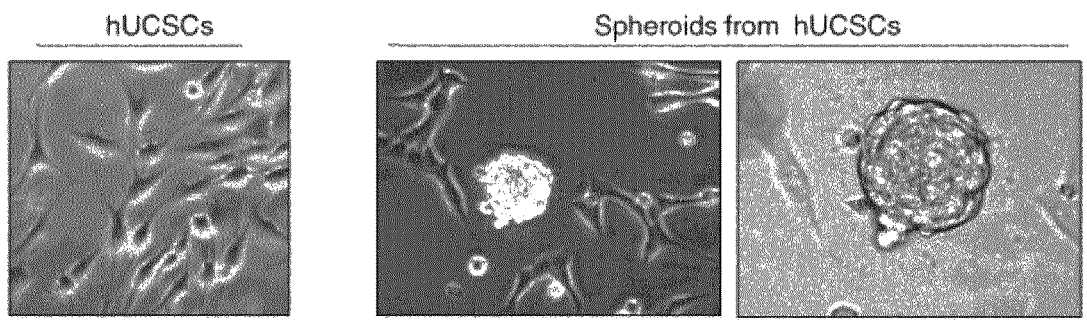

Human uterine cervical stem cells (hUCESCs) obtained from exfoliation of the uterine cervix were examined for immune phenotype using immunocytochimestry and flow cytometry. As shown in FIG. 1A, hUCESCs are positively immunolabeled with β-catenin, and vimentin antibodies, and some diffuse focal cells also are positive to pan-cytokeratin antibody. In addition, hUCESCs have strong expression of three transcription factors characteristic of embryonic stem cells, i.e. OCT4, KLF4, and Sox2 (FIG. 1B). hUCESCs phenotype was also determined by flow cytometry. We found that these cells were positive for CD29, CD44, CD73, and CD90, while they were negative for CD34, CD45, CD133 (hematopoietic markers), CD117, CD31, TRA-1-81 (embryonic stem cell surface marker), and HLA-DR (FIG. 1C).

To further evaluate the characteristics of hUCESCs cells, they were induced to form spheroids. After seven days in culture, individual cells were maintained in suspension culture in serum-free conditioned medium. After seven days, the cells formed clonal spheroid structures (FIG. 1D).

Figure 2:
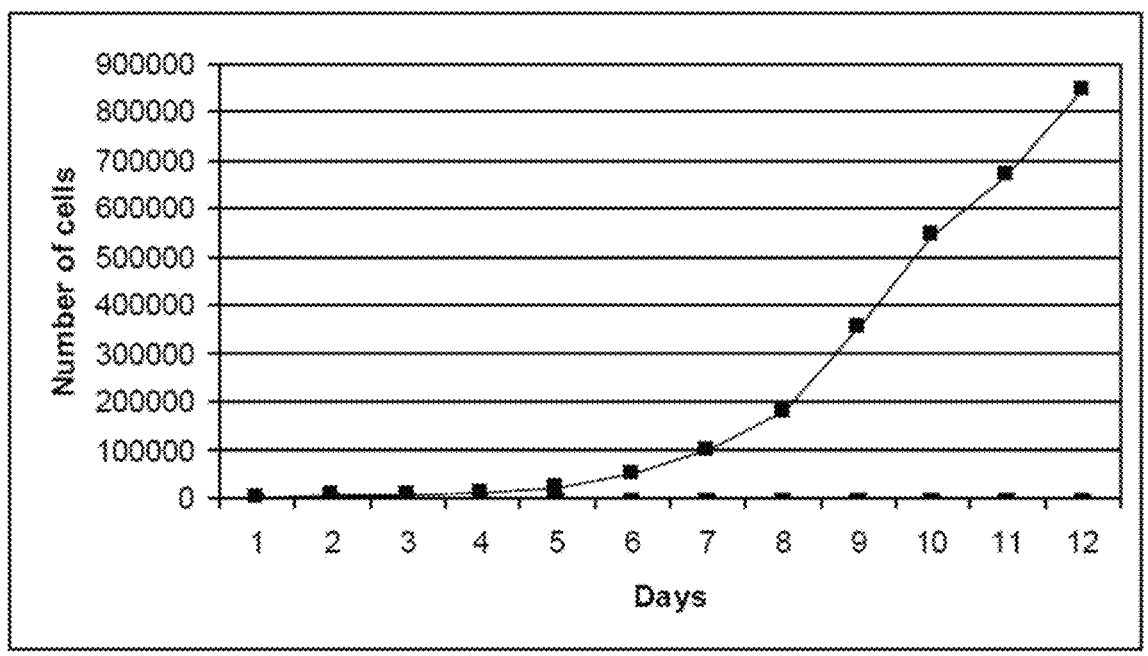
FIG. 2: Growth rate of hUCESCs. Growth of hUCESCs expressed as number of cells after seeding 2,000 cells/well.

Also, the rate of proliferation of hUCESCs was determined by counting the total number of cells in duplicate wells every day for 12 days. hUCESCs proliferate at a rate of 0.4-2.1 doublings per 24 hours (FIG. 2).

Example 2: Inflammation Related Experiments

I—Material and Methods

Immunogenicity Assay

The one-way mixed lymphocyte reaction (MLR) assay was used to determine the immunogenicity of human uterine cervical stem cells (hUCESCs). The MLR was performed in 96-well microtiter plates using RPMI 1640 medium without FBS. Peripheral blood mononuclear cells (PBMC) derived from two different donors were plated at $2 \times 10^5$ cells per donor per well. Different donors were used to maximize the chance that at least one of PBMC was a major mismatch to the hUCESCs test cells. Stimulator cells used in the assay included autologous PBMC (baseline response), allogeneic PBMC (positive-control response), and hUCESCs cell population. Stimulator cells were mitomycin C treated prior to being added to the culture wells ($2 \times 10^4$ cells per well, 10% stimulators cells). Additional controls cultures consisted of PBMC plated in medium alone (no stimulator cells), concanavalin A (ConA) stimulated PBMC and of hUCESCs mitomycin C treated alone. Triplicate cultures were performed for each treatment. Proliferation was assessed by cell proliferation reagent WST-1 (Roche applied bioscience). Living (metabolically active) cells reduced tetrazolium salts to colored formazan compounds; dead cells do not. Thus, tetrazolium salt-based colorimetric assays detect viable cells exclusively. The absorbance of the samples was measure against a background control as blank using a microtiter plate reader. The wavelength for measuring the absorbance of the formazan product is between 420-480 nm (max. absorption at about 440 nm). The reference wavelength should be more than 600 nm.

Inhibition of Monocytic Differentiation

U937 cell line was used for this test. Cells were plated in a 24 wells-plate at a density of $1.5 \times 10^5$ cells/well in DMEM:F12 with 10% FBS and antibiotics. 2 ng/mL of phorbol 12-myristate 13-acetate (PMA) was added, PMA treatment, which activates protein kinase C, induce a greater degree of differentiation in U937 cells as reflected by increased adherence and expression of surface markers associated with macrophage differentiation. In control wells no PMA solution was added. After 24 hours, medium was changed for conditioned medium from hUCESCs or from human adipose-derived stem cells (ASCs, StemPro®, Invitrogen), in the test wells for another 24 hours. Additional test consisted of stimulated U937 cell line with PMA in presence of conditioned medium. Supernatant was collected and adherent cells were washed, trypsinized and collected in the correspondent tube. Cells were centrifuged 5 min at 200 g and were resuspended in 100 µl of PBS. Differentiation to macrophages was monitored by the expression of monocyte differentiation marker CD11 b by flow cytometry analysis. Cells were stained with PE-CD11 b monoclonal antibody and with 7-AAD to assess cell viability. The Mac-1 (CD11 b) antigen was originally described as a cell surface marker for macrophages. The Mac-1 antigen mediates the attachment and phagocytosis of particles coated with C3bl by granulocytes and macrophages. In addition, Mac-1 appears to mediate a wide variety of adhesion dependent functions, including granulocyte chemotaxis, adherence to surfaces and aggregation.

Inhibition of PBMC Proliferation with Conditioned Medium

Peripheral blood mononuclear cells (PBMC) from healthy volunteers were isolated from 20 mL heparinized peripheral blood by Histopaque-1077 (Sigma) density gradient centrifugation. Cells recovered from the interface were washed twice with PBS and resuspended in supplemented RPMI 1640. PBMC viability was determined by trypan blue exclusion. Aliquots of the isolated PBMC were frozen and stored at $-80°$ until further use. For experiments, frozen aliquots of the PBMC were randomly chosen from the 8 unrelated donors, thawed and used.

For assaying PBMC proliferation, isolated PBMC were cultured ($2 \times 10^5$ cells/well) for 4 days in 96-well flat-bottomed microtiter plates in DMEM:F12 without FBS, with conditioned medium (from hUCESCs or ASCs) and stimulated with 1 µg/mL concanavalin A (ConA). PBMC alone and ConA stimulated PBMC with $10^{-6}$ M dexamethasone served as basal proliferation control and inhibition control, respectively. Proliferation was assessed by cell proliferation reagent WST-1. This assay detects viable cells exclusively. The absorbance of the samples was measure against a background control as blank using a microtiter plate reader.

II—Results

Figure 3:
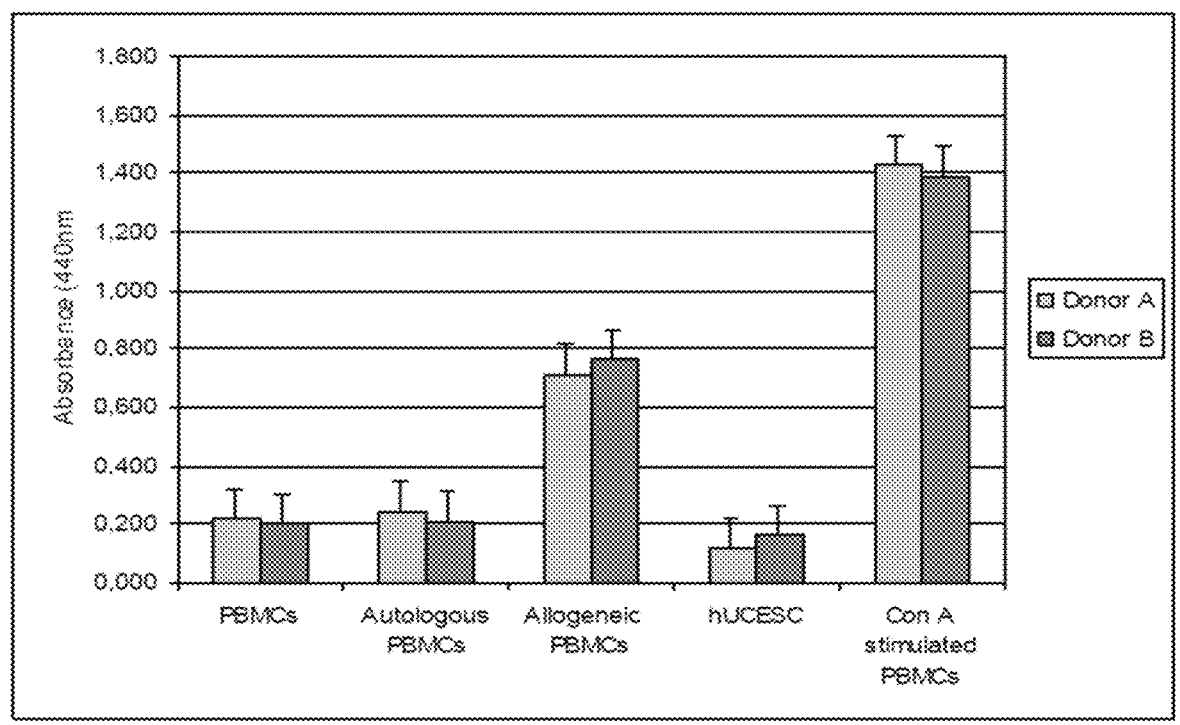
FIG. 3: Immunogenicity assay. The figure displays a representative MLR from two donors. The proliferation of PBMCs was determined in the absence of stimulator cells, in the presence of autologous mitomycin C treated PBMCs (negative control), in the presence of allogeneic mitomycin C treated PBMCs (positive control), in the presence of mitomycin C treated hUCESCs, and Con A stimulated PBMCs (positive control). The stimulator cells were tested at density of $2\times10^4$ per well. One-way MLR assays were performed to assess the immunogenicity of hUCESCs. The proliferation of PBMCs was measured based on the increased number of metabolically active living cells in the presence of mitomycin C treated stimulator cells. Autologous and allogeneic PBMCs served as negative and positive stimulator cell controls, respectively. Con A stimulated PBMCs served as another positive stimulation control cells. hUCESCs did not induce T cell proliferation in MLR assays.

One-way MLR assays were performed to assess the immunogenicity of hUCESCs. The proliferation of PBMCs was measured based on the increased number of metabolically active living cells in the presence of mitomycin C treated stimulator cells. Autologous and allogeneic PBMCs served as negative and positive stimulator cell controls, respectively. ConA stimulated PBMCs served as other positive stimulation control cells. As shown in FIG. 3, hUCESCs did not induce T cell proliferation in MLR assays.

Figure 4:
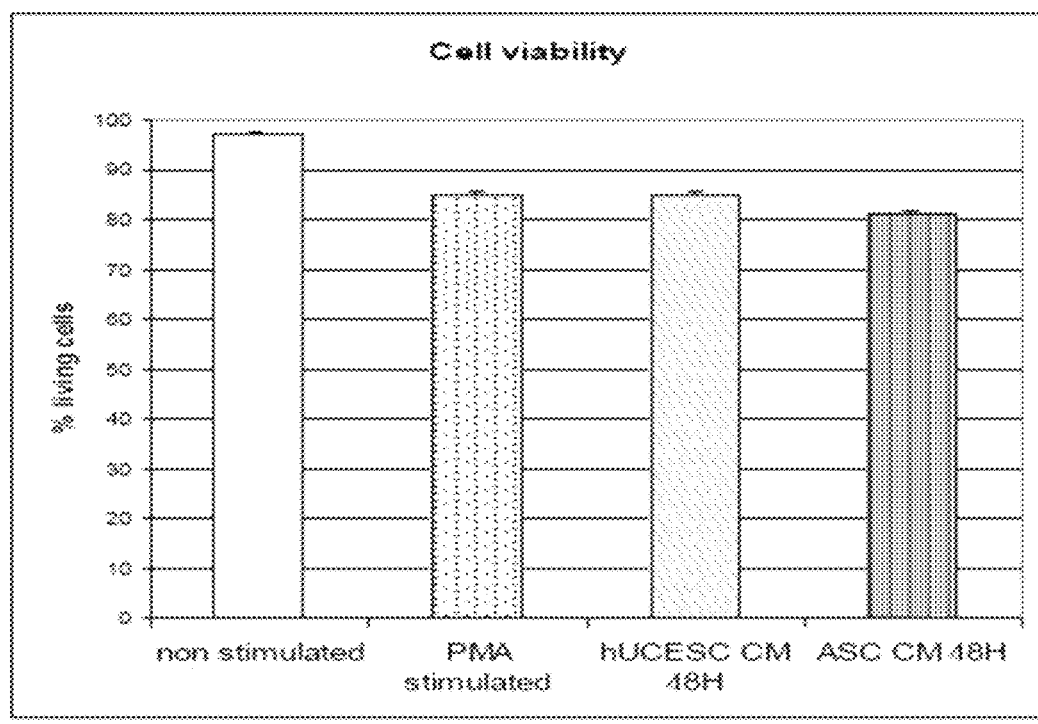
FIG. 4: Inhibition of monocytic differentiation with stimulation in presence of hUCESCs conditioned medium. A) The viability of the U937 cells is higher than 80%. B) Effect of hUCESCs and ASCs conditioned medium on the expression of a macrophage differentiation marker. Basal level of U937 CD11 b expression is 34%. Compared with the PMA treated control U937 cells, the percentage of cells stained positive for CD11b decreased from 73% in PMA treated U937 cells to 48% in hUCESCs conditioned medium treated U937 cells.
Figure 4:
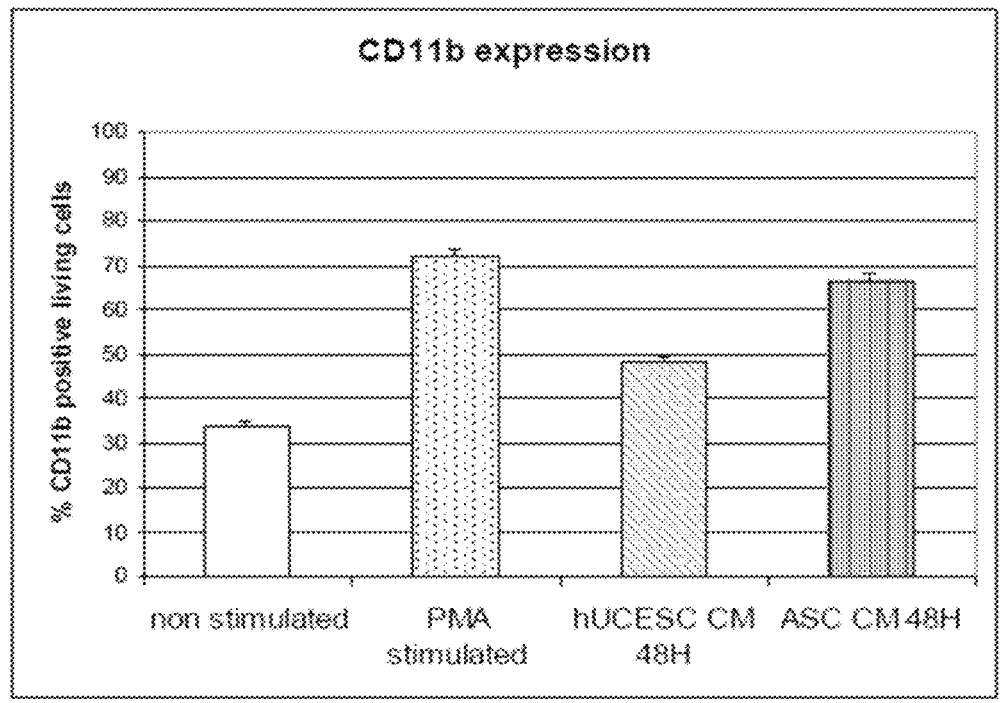

In addition, differentiation to macrophages was monitored by the expression of monocyte differentiation marker CD11b by flow cytometry analysis. In FIG. 4, it was shown the inhibition of monocytic differentiation with stimulation in presence of hUCESCs conditioned medium. Basal level of U937 CD11 b expression was 34% and compared with the PMA treated control U937 cells, the percentage of cells stained positive for CD11 b decreased from 73% in PMA treated U937 cells to 48% in hUCESCs conditioned medium treated U937 cells. The percentage of CD11b expression for U937 cells treated with ASCs conditioned medium was 67%. It is worth noting that the viability of the U937 cells, in all conditions, was higher than 80%. These data indicate an inhibition or protection of monocyte differentiation in the presence of hUCESCs conditioned medium. In FIG. 5, it is shown the inhibition of monocytic differentiation: stimulation during 24 hours and addition of hUCESCs conditioned medium. Basal level of U937 CD11 b expression was 38% and compared with the PMA treated control U937 cells, the percentage of cells stained positive for CD11 b decreased from 82% in PMA treated U937 cells to 48% in U937 cell treated with hUCESCs conditioned medium produced during 24 hours (CM 24 hours), and to 34% in U937 cell treated with conditioned medium produced during 48 hours (CM 48 hours). Nevertheless the CD11b expression in ASCs CM 48 hours treated U937 cells was 77%. It is worth noting that the viability of the U937 cells, in all conditions, was higher than 80%. These data indicate an inhibition of monocyte differentiation in the presence of hUCESCs conditioned medium and in the case of 48 hours conditioned medium the percentage of CD11 b positive cells was appreciably the same of U937 basal level.

In FIG. 6, it is shown the inhibition of PBMCs proliferation with conditioned medium. Both hUCESCs conditioned media, 24 hours and 48 hours, suppressed PBMCs proliferation. The suppression was more effective with hUCESCs conditioned medium than ASCs conditioned medium. The magnitude of suppression by hUCESCs conditioned medium exceeded that of dexamethasone. Dexamethasone is the more potent anti-inflammatory drug, these data suggest the high anti-inflammatory potential of hUCESCs conditioned medium.

Example 3: Cancer Related Experiments

I.—Material and Methods

Cell Cultures

MCF-7 and MDA-MB-231 cells (human breast adenocarcinoma cell lines) were obtained from the European Collection of Cell Cultures (Salisbury, Wilts., UK) and HT29 (colorectal adenocarcinoma cell line) and AGS (gastric adenocarcinoma cell line) were obtained from the American Type Culture Collection (ATCC, Manassas, VA, USA). These cell lines were grown in 90-mm Petri dishes in DMEM supplemented with 10% FBS, 100 U/mL penicillin and 100 μg/mL streptomycin in an air-$CO_2$ (95:5) atmosphere at 37° C. Confluent cells were washed twice with phosphate-buffered saline and harvested by a brief incubation with trypsin-EDTA solution (Sigma-Aldrich, St. Louis, MO, USA) in PBS. Human cervical uterine stem cells (hUCESCs, obtained as above described), primary cultures from human breast tumours, and human adipose-derived stem cells (ASCs, StemPro®, Invitrogen), were grown in 90-mm Petri dishes in DMEM-F12 (1:1) supplemented with 10% FBS, 100 U/mL penicillin, and 100 μg/mL streptomycin in an air-$CO_2$ (95:5) atmosphere at 37° C.

Conditioned medium (CM) from hUCESCs, ASCs, MCF-7, and MDA-MB-231 was obtained by culturing the cells to 70% confluence in DMEM-F12 (10% FBS). Then cells were washed three times in PBS, and cultured again in DMEM-F12 without FBS. After 24 or 48 hours, medium was centrifuged for 10 minutes at 300 g, supernatant collected, and used immediately.

Three-dimensional cell culture was performed. Briefly, culture slides were coated with 60 μL of ice-cold Matrigel (BD Biosciences) and incubated at 37° C. for 20 minutes to allow the Matrigel to solidify. Cells were treated for 5 minutes with 0.25% trypsin-EDTA solution (2.5 g/L of trypsin, 0.38 g/L of EDTA) (Invitrogen). A single-cell suspension containing $5\times10^3$ cells per 100 μL volume of medium, supplemented with 2% (vol/vol) of Matrigel, was carefully placed on top of the solidified Matrigel. Incubation was carried out at 37° C. for 30 minutes to allow the cells to attach to the Matrigel. The culture slides were then placed in six-well plates, 500 μL of medium was added per well, and the cells were cultured for 10 days. hUCESCs were then treated with different media (DMEM-F12 with 10% FBS (+FBS), DMEM-F12 without FBS (−FBS), or 48 hours-conditioned medium from hUCESCs) for 1 week. Phase contrast photographs of cells as monolayers, or in three-dimensional cultures, were taken with an Olympus DP72 camera. Quantitation of sphere diameter was performed manually by tracing a straight line across the diameter of the sphere and scoring its value as arbitrary length units.

Co-Cultures

Cells were cultured as described above. Medium was removed at 70% confluence and cells labeled with pre-warmed CellTracker™ solution (MCF-7 and MDA-MB-231 with CellTracker™ GREEN CMFDA, and hUCESCs with CellTracker™ RED CMPTX; Invitrogen, Eugene, USA) as per the manufacturer's instructions. Then, $1\times10^5$ MCF-7 or MDA-MB-231 cells/well were plated at in 6-well plates, and four hours later $1\times10^5$ hUCESCs cells were added to the MCF-7 or MDA-MB-231 cells and co-cultured during 72 hours. Images were randomly photographed at 12, 48 and 72 hours with a high-resolution digital camera (Olympus DP 72; Olympus Corp., Tokyo, Japan). A counting frame (102 μm$^2$) was superimposed on the captured image, and only clearly visible cells were counted in at least three different fields on the photomicrographs, using the ImageJ software (National Institutes of Health, Bethesda, MD, USA).

Colorectal and Gastric Adenocarcinoma Cell Line Proliferation

HT29 and AGS proliferation was assessed using cell proliferation reagent WST-1 (Roche). HT29 and AGS cell line were plated at $2\times10^4$ cells per well in 96-well flat bottom microtiter tissue culture plates. Twenty-four hours later, cells were treated with equal volumes (150 µL) of DMEM-F12 with 10% FBS (control), DMEM-F12 without FBS (w/o FBS), and 24 or 48 hours-conditioned medium from hUC-ESCs, ASCs during 24 or 48 hours. WST-1 reagent (15 µL) was added to each well, and the mixture was incubated for 1 hour. The absorbance (440 nm) was measure against a background control as blank using a microtiter plate reader.

MTT Metabolization

Cell viability/proliferation experiments were carried out using 3-(4,5-dimethylthiazol-2-yl)-2,5-diphenyltetrazolium bromide (MTT) assays. MCF-7, MDA-MB-231, or primary cultures from human breast tumours were plated at a $3 \times 10^4$ cells per well in 24-well plates. Twenty-four hours later, cells were treated with equal volumes (500 µL) of DMEM-F12 with 10% FBS (+FBS), DMEM-F12 without FBS (−FBS), and 24 or 48 hours-conditioned medium from MCF-7, MDA-MB-231, hUCESCs, ASCs, or primary cultures of breast cancer tumours during 24 or 48 hours. MTT (0.5 µg/µL) was added to each well, and the mixture was incubated for 1 hour. The medium was then removed, and DMSO (500 µL) added to each well. Absorbance of samples was measured at 570 nm in a multiwell plate reader (Tecan ULTRA Evolution, Männedorf, Switzerland). Results were plotted as the mean±SD values of quadruplicates from at least two independent experiments.

Western Blot Analysis

MCF-7, MDA-MB-231 cells, and primary cultures from human breast tumours were lysed at 4° C. in 300 µL of lysis buffer (50 mM HEPES, pH 7.5; 150 mM NaCl; 5 mM EGTA; 1.5 mM MgCl$_2$; 1% SDS; 10% glycerol; 1% Triton X-100; 10 mM sodium orthovanadate; 4 mM PMSF, and 50 µg/mL aprotinin). The cell lysate was then centrifuged at 14,000×g for 5 minutes at 4° C., the resulting supernatant was collected, and protein concentration determined by the Bradford method. Western blotting was carried out. Briefly, 60 µg of total protein was subjected to SDS-PAGE electrophoresis. Proteins were transferred to a nitrocellulose membrane, blocked, and immunolabeled overnight at 4° C. with a primary antibody (see Table 1), washed three times with PBS-Tween-20, and incubated with the appropriate secondary antibody for 1 hour. The signal was detected with the Pierce ECL Western blotting substrate (Thermo Scientific, Rockford, IL, USA), and visualized by placing the blot in contact with standard X-ray film, as per the manufacturer's instructions.

TABLE 1

| Primary antibodies | | |
| --- | --- | --- |
| Antigen | Source | Application |
| Desmin | Dako | ICC |
| CK (clone AE1/AE3) | Dako | ICC |
| Actin HHF35 | Dako | ICC |
| Active caspase-3 (asp175) | Cell Signaling | IHC, WB |
| p63 | Dako | ICC |
| Cyclin D1 (clone 7213G) | Santa Cruz Biotech | WB |
| Smooth muscle actin | Dako | ICC |
| E-cadherin (clone NCH-38) | Dako | ICC |
| KLF4 (clone B-9) | Santa Cruz Biotech | ICC |
| OCT4 (clone 7F9.2) | Millipore | ICC |
| Cleaved PARP | Cell Signaling | WB |
| Sox2 (clone SOX2-6) | Sigma-Aldrich | ICC |
| Cyclin A | BD Biosciences | WB |
| Cyclin B | Santa Cruz Biotech | WB |
| Cyclin E | Santa Cruz Biotech | WB |
| B-catenin (clone1) | Dako | ICC |
| Vimentin (clone V9) | Dako | ICC |
| GAPDH | Santa Cruz Biotech | WB |
| Caspase 8 (D391) | Cell Signaling | WB |
| Caspase 9 (clone C9) | Cell Signaling | WB |
| Caspase 12 | Cell Signaling | WB |
| Bim (clone C34C5) | Cell Signaling | WB |
| Bid | Cell Signaling | WB |

ICC: immunocytochemistry;
IHC: immunohistochemistry;
WB: Western blot

Cell Cycle and Apoptosis Assays

Cell cycle and apoptosis assays were carried out by using a Guava flow cytometer (Millipore Corporation, Billerica, MA, USA). Briefly, $2 \times 10^5$ cells/well were cultured in: a) DMEM-F12 (1:1) supplemented with 10% FBS, b) DMEM-F12 (1:1) without FBS, and c) Conditioned Medium, during 48 hours, harvested, fixed with 70% cold ethanol for 30 minutes, washed with PBS, and incubated with ribonuclease (100 µg/mL), and propidium iodide (PI, 50 µg/mL) for 30 minutes in darkness, for cell cycle evaluation. Apoptosis analyses were performed using Annexin V-FITC. Cells were harvested, washed twice with PBS, and resuspended in 1× binding buffer (0.1 M Hepes (pH 7.4), 1.4 M NaCl, and 25 mM CaCl$_2$). 5 µl of FITC-Annexin V was added and incubated for 15 minutes at room temperature in darkness. Finally, 400 µL of 1× binding buffer was added to each tube, and analyzed. Annexin V positive and PI negative indicate early apoptosis, while both Annexin V negative and PI positive indicate late apoptosis.

Cell Invasion Assay

Assays were performed in BD BioCoatMatrigel invasion chambers according to the manufacturer's instructions (BD Biosciences). Filters precoated with Matrigel were used for examining cell invasion. MDA-MB-231 cells were placed into the upper chamber in 0.5 mL of DMEM serum-free medium ($5 \times 10^4$ cells per filter). Conditioned Medium of hUCESCs from 48 hours of culture was placed in the lower chamber as a 20% FBS. After incubation for 22 hours, cells that had migrated to the lower surface of the filters were fixed in methanol for 2 minutes at room temperature, stained using crystal violet for 2 minutes, visualized and counted. Values for cell migration or invasion were expressed as the mean number of cells per microscopic field over four fields per one filter for duplicate experiments. Experiments were repeated three times.

Animal Studies

Female mice age-matched between 6-8 weeks, homozygous for the severe combined immune deficiency spontaneous mutation (CB17-Prkdc$^{scid}$, named SCID, Parc Recerca Biomedica, Barcelona, Spain) were used for xenografting studies. Thirteen SCID mice (6 controls and 7 treated) were injected subcutaneously with $3 \times 10^6$ MDA-MB-231 cells stably transfected with the pcDNA3-luciferase vector (MDA-MB-231-luc cells) into the left and right flanks. Fifteen days after cells injection, mice were injected intratumourally (150 µL) with 48 hours-conditioned medium (CM) from hUCESCs or with placebo every five days until day forty seven. After luciferin injection (150 mg/kg), tumour growth was monitored externally by luminescence using the In Vivo Imaging System (IVIS, Caliper Life Sciences, Alameda, CA, USA). An intensity map was obtained using the Living Image software (Caliper Life Sciences). The software uses a color-based scale to represent the intensity of each pixel (ranging from blue representing low to red representing high). One control and one CM-treated mouse were sacrificed at day 31, and tumours excised, fixed in 10% neutral buffered formalin for 24 hours and embedded in paraffin for histological and immunohistochemistry studies. All remaining mice were monitored for survival analyses.

Immunohistochemistry

Mouse tumours were immersion-fixed in 10% neutral buffered formalin for 24 hours and embedded in paraffin routinely. Sections 4 µm thick were mounted on Flex IHC microscope slides (Dako, Glostrup, Denmark). The immunohistochemical (IHC) technique was automatically performed in an AutostainerLink 48 (Dako). An activated caspase 3 antibody (Cell signalling) was employed. Epitope retrieval was performed in a microwave 20 minutes using EnVision FLEX target retrieval solution (pH 9). All antibodies were incubated for 20 minutes at RT. As detection system we used EnVision FLEX/HRP Dako (dextran polymer conjugated with horseradish peroxidase and affinity-isolated goat anti-mouse and anti-rabbit immunoglobulins) for 20 minutes.

II—Results

Effect of hUCESCs on Proliferation of Human Cancer Cells

To explore the possible effect of hUCESCs on cancer cell line, cell proliferation assay was assessed on colorectal (HT29) and gastric (AGS) adenocarcinoma cell line treated during 48 hours with complete medium (control), incomplete medium (w/o FBS), conditioned medium from hUCESCs produced during 24 hours or 48 hours and conditioned medium from ASC produced during 48 hours. The effect of hUCESCs conditioned medium on colorectal and gastric adenocarcinoma cell proliferation was more potent that conditioned medium from ASC (FIG. 7A).

To explore the possible effect of hUCESCs on breast cancer after administration of conditioned medium (CM) from hUCESCs, the proliferation/cytotoxicity in the non-invasive human breast cancer cell line MCF-7 and in the highly invasive human breast cancer cell line MDA-MB-231 were evaluated. As shown in FIG. 7B-C, after 24 and 48 hours of administration of CM from hUCESCs (of 24 or 48 hours) to MCF-7 cells, no significant decrease of MTT metabolization was observed, as compared to cells treated with medium without FBS, or CM produced at 24 or 48 hours by MCF-7 cells. However, when the same CM from hUCESCs is administered to the MDA-MB-231 cell line, a significant decrease in cell proliferation is seen at 24 hours (CM from hUCESCs cultured during 48 hours, P<0.01) and 48 hours (CM from hUCESCs cultured during 24 and 48 hours, P<0.01 and P<0.001, respectively) (FIG. 7D-E). To evaluate whether the effect of CM from hUCESCs on cell proliferation could be maintained by co-culture of hUCESCs with MCF-7 or MDA-MB-231 cells or is dependent only on CM, MCF-7 and MDA-MB-231 cells were labeled with a green dye, and hUCESCs were labeled with a red dye. It was found that while MCF-7 cells co-cultured with hUCESCs grew as MCF-7 cultured alone (FIG. 7F), co-culture of MDA-MB-231 cells with hUCESCs significantly (P<0.01) reduced the number of MDA-MB-231 cells, as compared with growth of MDA-MB-231 cells alone (FIG. 7G).

Conditioned Medium from hUCESCs Delays Cell Cycle and Induces Apoptosis in MDA-MB-231 Cell Line Given that CM from hUCESCs significantly decreased proliferation of MDA-MB-231 cells, the cell cycle and apoptosis as possible mediators of this decrease were evaluated. MDA-MB-231 cells were cultured during 48 hours with DMEM plus 10% FBS (+FBS), DMEM without FBS (−FBS), or CM of 48 hours from hUCESCs, and then we performed flow cytometry using propidium iodide (PI) (to evaluate cell cycle), and annexin V/PI to evaluate apoptosis. In addition, Western blots were carried out to evaluate expression of proteins involved in both cell cycle and apoptosis. The results indicate that CM-treated cells significantly increases G0-G1 phase in relation to cells treated with complete (+FBS) or incomplete (−FBS) medium (FIG. 8A). Therefore, a visible decrease in cyclin A, cyclin B, and cyclin D1 protein expression was observed in CM-treated cells (FIG. 8B). Treatment of MDA-MB-231 cells with CM induced a significant increase of Annexin+/PI−, and Annexin+/PI+ cells vs cells cultured without FBS, suggesting that CM induces early and late apoptosis, respectively (FIG. 8C). Immunoblots of protein extracts from MDA-MB-231 cells treated with CM showed a clear increase in caspase-8, -12, -9, activated caspase-3, and cleaved PARP (FIG. 8D), and a decrease of Bid and Bim (FIG. 8E), with respect to cells treated with complete (+FBS) and incomplete (−FBS) medium.

Invasion, 3-D Cultures Formation, Tumor Growth, and Survival Rate is Modified by Conditioned Medium from hUCESCs It was explored whether CM from hUCESCs affected invasion of MDA-MB-231 cells through a matrigel matrix. FIG. 9A shows a significant (P<0.001) decrease of invading capacity of MDA-MB-231 cells in presence of CM, as compared with cells in presence of incomplete medium (−FBS). The three-dimensional growth of MDA-MB-231 cells was also explored. For these experiments, MDA-MB-231 cells were cultured in matrigel, a semisolid medium in which they form spherical structures. Treatment with the CM showed a substantial decrease in the diameter of these spheres, which was not appreciable when the cells were treated with incomplete medium (CM, mean diameter=2.8±1.0 vs −FBS, mean diameter=5.7±1.6, arbitrary units, P=0.023) (FIG. 9B).

The effect of intratumoral administration of CM in vivo using the severe immunodeficient (SCID) mouse tumor xenograft model was next evaluated. Mice were injected with MDA-MB-231 cells stably transfected with the luciferase vector in the mammary fad pad and 15 days later, when the tumor becomes visible, they were injected intratumorally, five days each, either with incomplete medium (controls) or with CM from hUCESCs (150 µl), and monitored externally by luminescence (FIG. 9C). A significant decrease (P=0.011) in tumor volume was observed after 15 days of treatment with CM (at day 30) (FIG. 9D). On day 33, two animals (one control and one CM-treated mice) were sacrificed, the tumors removed, and analyzed by immunohistochemistry for activated caspase-3 (as indicator of apoptosis). FIG. 9E shows a significant increase of activated caspase-3 expression in CM-treated mice. To evaluate the survival rate of mice, the remaining mice were injected each 5 days either with CM or with placebo, and observed until day 47. As shown in FIG. 9F, Kaplan-Meier survival plots indicate that mice treated with CM had a longer overall survival compared with control mice (P=0.019).

Conditioned Medium Reduces Proliferation in Tumors with High Proliferation Rate

The effect of administration of CM from hUCESCs in primary cultures from patients with breast tumors was next evaluated. Thus, ten breast cancer primary cultures were evaluated for cell proliferation using a MTT assay. While in breast tumoral cells with low proliferation rate (11B3186, 11B2445, 11B530, 11B545, 11B980, and 11B2127) administration of CM from hUCESCs had no significant effect on cell proliferation compared with the effect produced by incomplete medium (−FBS), CM from itself, or CM produced by adipose-derived stromal cells (ASCc) in primary cultures from breast tumors with higher proliferation rate (11B512, 11B3285, 11B3171, and 11B7352), administration of CM from hUCESCs induced a significant (P<0.001) decrease in cell proliferation as compared with other treatments (FIG. 10A). The cyclin D1 and cleaved PARP expression in protein extracts from these primary tumors with higher proliferation rate was also evaluated. The results are shown in FIG. 10B. A clear decrease in expression of cyclin D1 and PARP cleavage was observed when CM from hUCESCc was administered, but not in primary cultures treated with incomplete medium (without FBS).

Example 4: Growth Inhibition of Pathogenic Microorganism by hUCESCs

I—Material and Methods

Bacterial strains used were: *E. coli* (ATCC 25992), *Staphylococcus aureus* (ATCC 29213), and *Enterococcus faecalis* (ATCC 51299).
Growth Inhibition in Multiwell Plates by Serial Dilution Growth inhibition of pathogenic microorganism was assessed in 96 microwell plates cultures to determine the maximum dilution of medium with antimicrobial activity. Briefly, 100 µl of serial 1:2 dilutions and 75 µl of serial 1:2 dilutions of control (DMEM-F12 medium without FBS) and conditioned medium (hUCESCs or adipose tissue-derived MSC) were placed in 96 wells plates. Then, the bacterial suspension in brain heart broth (1:300 dilution of 0.5 McFarland suspension) was added to each well. Plates were incubated at 37° for 24 to 48 h. Bacterial growth inhibition was determined by comparing control wells to wells which contain hUCESCs or adipose tissue-derived MSC conditioned medium.
Inhibition of Bacterial Growth by hUCESCs and its Conditioned Medium For each experiment *Escherichia coli* (*E. coli*, ATCC 25992) colonies were seeded from frozen stocks, and grown overnight at 37° C. in liquid Luria-Bertani (LB) medium (Difco BD, USA) with slight agitation. Before each experiment, bacterial cells were washed once and resuspended in PBS, and optical density (OD at A=600 nm) of the suspension was measured. Number of CFU was calculated as according to the following equation: $OD_{600}=1.0$ corresponds to $4\times10^8$ CFU/ml for *E. coli*. Assessment of direct inhibition of bacterial growth by hUCESCs or its conditioned medium (CM) was done by counting CFU and reading OD.

Briefly, in 24-well plates, 300 CFU *E. coli* were added to: a) $2\times10^5$ hUCESCs in DMEM/F-12-HAM (1:1) supplemented with 10% FBS, b) $2\times10^5$ normal human fibroblasts (NHF) in the same culture medium, and c) culture medium alone. Then, cultures were incubated for 6 hours in humidified CO2 incubator. Optical density was measured after 2 h growing infected cultures in LB at 37-C. CFU quantification was done in LB-agar plates after overnight incubation at 37° C. The remaining infected medium was centrifuged at 15,000 rpm for 10 min and frozen at −20° C. (to eliminate any residual bacterial organisms). Samples were thawed on ice, and aliquots were transferred to a 96-well plate, inoculated with 100 CFU *E. coli* and incubated for 16 hours at 37° C. Then OD and CFUs were counted as described above.

II—Results

Growth Inhibition in Multiwell Plates by Serial Dilution

All dilutions of control medium showed a bacterial growth. Adipose tissue-derived MSC conditioned medium showed no antimicrobial activity, although hUCESCs conditioned medium showed an inhibition of bacterial growth up to 1/20 dilution (FIG. 11).
Inhibition of Bacterial Growth by hUCESCs and its Conditioned Medium Human hUCESCs significantly (p<0.001) inhibited *E. coli* bacterial growth compared with both control medium and control NHF cells. Both CFU and OD quantification showed a decrease of around 50% in number of colonies (FIG. 12) and absorbance (FIG. 13) respectively compared with controls (medium alone and NHF). The infected medium derived from the hUCESCs showed the same effect against *E. coli* as the hUCESCs. These results suggest that the antibacterial effect is produced by some soluble factor secreted by the hUCESCs.

Example 5: Tissue Regeneration Related Experiments: Alkali Corneal Epithelial Wound Healing in a Rat Model of Dry Eye by hUCESCs Conditioned Medium I—Material and Methods 15 female Sprague-Dawley rats weighing 200-250 g were used to do this experiment. All animals were anesthetized by intraperitoneal injection of a mixture of ketamine (0.425 ml) and xilacine (0.2 ml) soaked in NaOH (0.375 ml). At the end of the experiment, all rats were sacrificed by CO2 inhalation.
Dry Eye Model 3 out of 15 rats were kept with healthy eyes, the remaining 12 rats were anesthetized and the extraocular lacrimal gland was excised bilaterally to create dry eyes. The extraocular lacrimal gland is one of the three lacrimal glands of the rat. This gland is the main gland for tear production and with an easy access (FIG. 14A). One week after the surgery, tear production was measured with the Schirmer Test (Laboratorios Cusí SA, Barcelona). The paper strips were adapted by cutting them 2 mm wide. The tip of the strip was folded at 1 mm length and introduced under the eyelid during 5 minutes. After this time, the length of the wetted strip from the folded mark (FIG. 14B, C) was measured. All 12 rats have presented dry eyes.
Corneal Alkali Wound and Examination A central corneal alkali wound was produced in both eyes by applying a piece of Whatman paper (2×2 mm) soaked in 2 µl NaOH (1 mol/1) for 60 seconds. The cornea was then rinsed with saline during 30 seconds. All rats were previously anesthetized as described above. The damaged epithelium was visible after fluorescein (Colircusí Fluoresceina, Alcon Cusí, S. A., El Masnou-Barcelona) staining of the surface of the cornea in the anesthetized rat. The cornea was photographed with a digital camera (Nikon D200, Tokio, Japón) attached to a surgical microscope (Takagi OM-5 220-2, Tokio, Japón) under blue light.

Quantitative measurements of the corneal injury were made on the photograph off line with the free commercial software ImageJ (Softonic International, SL) by counting the number of pixels colored with the fluorescein with respect to the total number of pixels of the surface of the eye.

Groups and Treatments

Fifteen rats where divided into 5 groups of 3 rats each. There was one group with healthy eyes (group Normal) and no corneal lesion and 4 groups (groups CM, M, SH and No Treat) with dry eyes and corneal alkali burn in both eyes.

Treatments consisted on topical applications of eye drops dosed 4 times per day of: Group CM: Conditioned Medium. Group M: Culture Medium (DMEM-F12; Gibco, Life Technologies, Paisley, UK) without any previous contact with cells.

Group SH: Ophthalmic drops with sodium hyaluronate (0.015 g/10 mL).

Group No Treat: No Treatment.

Conditioned Medium (CM)

Human uterine cervical mesenchymal stem cells (cells of the invention) were cultured in 90-mm Petri dishes of 70% confluence with 5 ml of DMEM-F12 (Gibco, Life Technologies, Paisley, UK) culture medium, in air-C02 (95:5) atmosphere at 37° C. during 48 h. After this time, sobrenadant is collected, frozen and liofilized to store at −80° C. until used. The liofilized powder was resuspended just before used in ddH$_2$O.

Histology

At the end of the experiment, 5 days after the corneal alkali burn, one rat randomly selected from each group was sacrificed, the eyeball excised and immersion-fixed in 10% neutral buffered formalin. After 24 h, the cornea was dissected from the eyeball and immersed in Ethanol (70%). The cornea was then embedded in paraffin and 20 µm sections were mounted and stained with hematoxylin-eosin (H-E) for histological evaluation.

mRNA Expression Analysis

At the end of the experiment, 5 days after corneal lesion, the two remaining rats from each group were sacrificed and the corneas dissected. The mRNA expression levels of macrophage inflammatory protein-1 alpha (MIP-1α), monocyte chemotactic protein-1 (MCP-1) and tumor necrosis factor-alpha (TNF-α) in the corneas were evaluated using real time polymerase chain reaction (real-time PCR). Total RNA was isolated from the corneas using TRIzol (Invitrogen). cDNA was synthesized from the RNA (1 µg) in a 30 µl reaction with Transcriptor First Strand cDNA Synthesis Kit (Roche Diagnostics). Reactions of quantitative Real Time PCR were done with 2 µg cDNA in a 20 µl volume using iQ SYBRGreen Supermix (Bio-Rad) on iCycler equipment (7500 PCR Systems, Applied Biosystems-Life Technologies). Samples were denatured at 94° C. for 10 sec, annealed at 58° C. for 10 sec and extended at 72° C. for 10 sec for a total of 35 cycles. Samples were quantified using Sequence Detection Software 1.4 (Applied Biosystems), with β-actin as the endogenous control. The oligonucleotide sequences are described in Table 2.

TABLE 2

Primer sets for real-time PCR.

| Gene | Forward primers (5'-3') | Reverse primers (5'-3') |
|---|---|---|
| MIP-1 α | ATGAAGGTCTCCACCACTGC (SEQ ID No. 1) | AAAGGCTGCTGGTCTCAAAA (SEQ ID No. 2) |
| MCP-1 | ATGCAGTTAATGCCCCACTC (SEQ ID No. 3) | TTCCTTATTGGGGTCAGCAC (SEQ ID No. 4) |
| TNF-α | TCAGTTCCATGGCCCAGAC (SEQ ID No. 5) | GTTGTCTTTGAGATCCATGCCATT (SEQ ID No. 6) |
| β-actin | GGAGATTACTGCCCTGGCTCCTA (SEQ ID No. 7) | GACTCATCGTACTCCTGCTTGCTG (SEQ ID No. 8) |

Data Analysis

Values are expressed as mean±standard deviation. Means were compared using one-way ANOVA, with the Tukey's range test for post hoc comparisons. P values of less than 0.05 were considered statistically significant. The MATLAB R2011a Version7.1 (MathWorks, Inc) software was used for all calculations.

The percentage of epithelial regeneration (% ER) was calculated with the formula:

$$\% \ ER = 100(m_i - m_f)/m_i$$

Where $m_i$ is the first measurement of the corneal injury (just after the alkali burn) and $m_f$ is the final measurement 48 hours after. Both measurements represent the percentage of wounded area with respect to the total area of the cornea.

II—Results

Effects on Epithelial Recovery

Corneal epithelial staining with fluorescein is indicative of epithelial defects (FIG. 15A). The percentage of epithelial regeneration (% ER) for each group was calculated as described in methods section. The recovery of the corneal surface was significantly faster in the group treated with CM than in the other groups 15 hours after the alkali burn (p<0.005, 1-way ANOVA; FIG. 15B). The means of the epithelial regeneration (ER) were: 62±5% for the group CM; 34±15% for the M group; 32±15% for the SH group and 36±13% for the NoTreat group. On day 5 after the alkali burn the recovery of the corneal surface was almost complete in all treated groups (>75%) but still significantly faster in the group treated with CM compared with the group without treatment (p=0.005, 1-way ANOVA; FIG. 15C). The means of the ER were: 92±4% for the group CM; 77±15% for the M group; 74±15% for the SH group and 62±16% for the NoTreat group.

Alkaline corneal epithelial wound closure on day 5, were compared after H-E staining of the cornea sections, the regeneration of the corneal epithelium is faster in the group treated with CM than in the others (FIG. 16).

Anti-Inflammatory Effects

To investigate the possible mechanism by which CM attenuate inflammation, we assessed the production of the chemotactic factors MIP-1α and MCP-1 and the immunostimulatory cytokine TNF-α. We found that levels of all MIP-1α, MCP-1 and TNF-α were very high in the M group (group treated with culture medium, with no contact with stem cells) compared with the rest of the groups, including the No Treat group (with lesion but no treatment) (p<0.05; 1-way ANOVA; FIG. 17). However, the group treated with the same culture medium but with previous contact with the stem cells (CM group), had lower levels of all MIP-1α, MCP-1 and TNF-α compared with the M group (p<0.05; 1-way ANOVA; FIG. 4). This result seems to indicate that the culture medium used (DMEM-F-12) has proinflammatory effects on this type of lesions and these effects were contrarested by some of the factors secreted by the cultured stem cells. In addition, Levels of MIP-1α in the CM group are similar to those in the No Les group (without corneal lesion), and lower than the other treated groups (M and SH) and the No Treat group (p<0.05; 1-way ANOVA; FIG. 17B). This result is indicative of an anti-inflammatory effect of the CM on the injured cornea.

Example 6: Experiments Related to Germ Cells Selection: Effect of hUCESC Conditioned Medium on Spermatozoa I—Material and Methods Conditioned medium (CM) was lyophilized and reconstituted at three concentrations 0.5:1, 1:1 and 4:1. Experiments were carried out on fresh semen and/or capacitated spermatozoa at 0 hours (TO), 3 hours (T3) and 24 hours (T24).

Semen Analysis

Semen analysis was performed according to 2010 World Health Organization (WHO) guidelines using light microscopy. After liquefaction, 5 μL of semen was loaded on a Neubauer counting chamber (Sefi Medical Instruments, Haifa, Israel). Total sperm count ($\times 10^6$/mL) and percentage motility were measured manually. A minimum of 200 cells were counted per 5 μL drop, and at least two drops were studied per sample. Sperm vitality was studied by a dye exclusion method, also following WHO guidelines, using eosin red and nigrosin.

Assessment of Oxidative Stress

Dihydroethidium (DHE) is a poorly fluorescent two-electron reduction product of ethidium ($Et^+$) that on oxidation produces DNA-sensitive fluorochromes that generate a red nuclear fluorescence when excited at 510 nm. The results obtained with this probe have been validated as a measure of the ability of human spermatozoa to generate ROS, including definitive identification of the superoxide anion. For the intracellular ROS production assay, DHE (3 μM) were diluted in PBS buffer and added to $0.5 \times 10^6$ fresh spermatozoa in a final volume of 500 μl. The cells were then incubated in the dark at RT for 45 min, washed twice (2000 rpm, 5 min) and the resultant red (HE) fluorescence was analyzed by flow cytometry using a FACScan analyzer. Data were expressed as the percentage of fluorescent spermatozoa.

Assessment of Plasma Membrane Integrity

The integrity of mitochondrial plasma membrane has been positive correlated with sperm motility and vitality, and negative correlated with cell apoptosis. During the process of oxidative phosphorylation, the protons are pumped from inside the mitochondria to the outside, creating an electrochemical gradient called the inner mitochondrial membrane potential (MMP). The ability to discriminate between mitochondria exhibiting high MMP from those having low MMP provides a rigorous estimation of the mitochondrial metabolic function and membrane integrity. The evaluation of MMP on spermatozoa was performed by flow cytometry using the 3,3'-dihexyloxacarbocyanine iodide ($DiOC_6$) fluorescent dye. Briefly, spermatozoa ($0.5 \times 10^6$) from each fresh sample were incubated with $DiOC_6$ (0.1 nM diluted in HTF medium) at 37° C. water bath for 45 minutes in a final volume of 500 μl. Then cells were washed twice (2000 rpm, 5 min) with PBS, resuspended in 500 μl PBS buffer and analyzed by flow cytometry. As a negative control, sperm sample was also incubated with 1 mM uncoupler carbamoyl cyanide m-chlorophenylhydrazone (CCCIP).

II—Results hUCESC conditioned medium (CM) shows an effect on sperm characteristics depending on concentration and time (Table 3). Compared to control (w/o CM), CM 4:1 shows a diminution of all percentages of sperm characteristics at T3 and T24, whereas CM 1:1 shows a higher effect on motility, vitality, oxidative stress and membrane potential at T24.

TABLE 3

Sperm characteristics depending on hUCESC conditioned medium concentration.

|  | Control (w/o CM) | semen with CM 1:1 | semen with CM 4:1 |
|---|---|---|---|
| T 0 | | | |
| Motility progression (%) | 37 | 35 | 36 |
| Total motility (%) | 51 | 53 | 53 |
| Sperm vitality (%) | 79 | 79 | 77 |
| Oxidative stress (%) | 18 | 15 | 17 |
| Mitochondrial membrane potential (%) | 57 | 53 | 58 |
| T 3 | | | |
| Motility progression (%) | 39 | 21 | 3 |
| Total motility (%) | 56 | 51 | 8 |
| Sperm vitality (%) | 67 | 62 | 10 |
| Oxidative stress (%) | 19 | 19 | 34 |
| Mitochondrial membrane potential (%) | 29 | 32 | 15 |
| T 24 | | | |
| Motility progression (%) | 30 | 3 | 1 |
| Total motility (%) | 42 | 8 | 4 |
| Sperm vitality (%) | 61 | 10 | 6 |
| Oxidative stress (%) | 27 | 48 | 52 |
| Mitochondrial membrane potential (%) | 26 | 8 | 4 |

Table 4 shows that hUCESC CM 1:1 shows a higher effect than hUCESC CM 0.5:1 on sperm characteristics of fresh ejaculate and capacitated spermatozoa. hUCESC CM shows a higher effect on fresh sperm than capacitated spermatozoa, this help to the selection of good quality spermatozoa.

TABLE 4

|  | Concentration 0,5:1 | | | | Concentration 1:1 | | | |
|---|---|---|---|---|---|---|---|---|
|  | Fresh | | Capacitated | | Fresh | | Capacitated | |
|  | 1 | 2 | 1 | 2 | 1 | 2 | 1 | 2 |
| T 0 | | | | | | | | |
| Motility progression (%) | 61 | 71 | 85 | 78 | 61 | 71 | 85 | 78 |
| Total motility (%) | 67 | 82 | 90 | 88 | 67 | 82 | 90 | 88 |
| Sperm vitality (%) | 71 | 77 | 94 | 89 | 71 | 77 | 94 | 89 |

TABLE 4-continued

| | Concentration 0,5:1 | | | | Concentration 1:1 | | | |
|---|---|---|---|---|---|---|---|---|
| | Fresh | | Capacitated | | Fresh | | Capacitated | |
| | 1 | 2 | 1 | 2 | 1 | 2 | 1 | 2 |
| Oxidative stress (%) | 35 | 24 | 13 | 21 | 35 | 24 | 13 | 21 |
| Mitochondrial membrane potential (%) | 64 | 60 | 68 | 59 | 64 | 60 | 68 | 59 |
| T 3 | | | | | | | | |
| Motility progression (%) | 57 | 71 | 76 | 68 | 41 | 58 | 80 | 60 |
| Total motility (%) | 63 | 80 | 89 | 76 | 59 | 70 | 88 | 68 |
| Sperm vitality (%) | 64 | 65 | 77 | 74 | 42 | 41 | 52 | 55 |
| Oxidative stress (%) | 40 | 25 | 14 | 14 | 17 | 30 | 38 | 28 |
| Mitochondrial membrane potential (%) | 61 | 68 | 79 | 78 | 74 | 62 | 32 | 64 |
| T 4 | | | | | | | | |
| Motility progression (%) | 4 | 7 | 26 | 12 | 3 | 1 | 5 | 2 |
| Total motility (%) | 9 | 9 | 45 | 27 | 15 | 2 | 24 | 10 |
| Sperm vitality (%) | 22 | 19 | 25 | 27 | 27 | 24 | 19 | 12 |
| Oxidative stress (%) | 51 | 47 | 21 | 44 | 36 | 69 | 58 | 68 |
| Mitochondrial membrane potential (%) | 45 | 41 | 61 | 39 | 51 | 23 | 31 | 20 |

The invention claimed is:

1. A method for the treatment or prevention one or more symptoms associated with disorders in which modulation of a subject's immune system is beneficial, wherein the disorders are selected from: cancer, precancerous lesions, inflammatory diseases, autoimmune diseases, chronic pathologies, infectious diseases or diseases associated to tissue loss, the method comprising the administration to a patient in need thereof a therapeutically effective amount of an isolated non-cancerous non-menstrual uterine cervix mesenchymal stem cell, a cell population comprising the isolated stem cell, or a conditioned medium obtained from the culture of said cell, wherein the isolated non-menstrual uterine cervix mesenchymal stem cell (a) expresses the cell markers CD29, CD44, CD73, CD90, CD105, vimentin, cytokeratin (CKAE1AE3), Klf4, Oct4, and Sox-2; (b) does not express CD34, CD117, p63, and at least one cell marker selected from the group consisting of desmin, actin HHF35, β-catenin, E-cadherin, CD133, HLA-DR, TRA1-81, CD45, and CD31.

2. The method according claim 1 wherein the isolated non-cancerous non-menstrual uterine cervix mesenchymal stem cell further shows: (c) a proliferating rate of from 0.4 to 2.1 doublings per 24 hours in growth medium; (d) capacity to grow in monolayer and to adhere to a substrate; and (e) a non tumorigenic capacity.

3. The method according claim 1 wherein the isolated non-cancerous non-menstrual uterine cervix mesenchymal stem cell further shows (f) a fibroblast-like morphology, (g) a stable karyotype for at least 10 cell passages, (h) capacity to be differentiated into an adipogenic, osteogenic, neural or myocytic cell linage, and/or (i) capacity to form spheres.

4. The method according claim 1 wherein the isolated non-cancerous non-menstrual uterine cervix mesenchymal stem cell further shows (f) a fibroblast-like morphology, (g) a stable karyotype for at least 20 cell passages, (h) capacity to be differentiated into an adipogenic, osteogenic, neural or myocytic cell linage, and/or (i) capacity to form spheres.

* * * * *

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: MIP-1 Forward primer (5 prime - 3 prime)

<400> SEQUENCE: 1
atgaaggtct ccaccactgc          20

<210> SEQ ID NO 2
<211> LENGTH: 20
<212> TYPE: DNA
<213> ORGANISM: Artificial Sequence
<220> FEATURE:
<223> OTHER INFORMATION: MIP-1 Reverse primer (5 prime - 3 prime)

<400> SEQUENCE: 2
aaaggctgct ggtctcaaaa          20

<210> SEQ ID NO 3
<211> LENGTH: 20
<212> TYPE: DNA
<213> ORGANISM: Artificial Sequence
<220> FEATURE:
<223> OTHER INFORMATION: MCP-1 Forward primer (5 prime - 3 prime)

<400> SEQUENCE: 3
atgcagttaa tgccccactc          20

<210> SEQ ID NO 4
<211> LENGTH: 20
<212> TYPE: DNA
<213> ORGANISM: Artificial Sequence
<220> FEATURE:
<223> OTHER INFORMATION: MCP-1 Reverse primer (5 prime - 3 prime)

<400> SEQUENCE: 4
ttccttattg gggtcagcac          20

<210> SEQ ID NO 5

-continued

```
<211> LENGTH: 19
<212> TYPE: DNA
<213> ORGANISM: Artificial Sequence
<220> FEATURE:
<223> OTHER INFORMATION: TNF-alpha Forward primer (5 prime - 3 prime)

<400> SEQUENCE: 5
tcagttccat ggcccagac                                                19

<210> SEQ ID NO 6
<211> LENGTH: 24
<212> TYPE: DNA
<213> ORGANISM: Artificial Sequence
<220> FEATURE:
<223> OTHER INFORMATION: TNF-alpha Reverse primer (5 prime - 3 prime)

<400> SEQUENCE: 6
gttgtctttg agatccatgc catt                                          24

<210> SEQ ID NO 7
<211> LENGTH: 23
<212> TYPE: DNA
<213> ORGANISM: Artificial Sequence
<220> FEATURE:
<223> OTHER INFORMATION: Beta-actin Forward primer (5 prime - 3 prime)

<400> SEQUENCE: 7
ggagattact gccctggctc cta                                           23

<210> SEQ ID NO 8
<211> LENGTH: 24
<212> TYPE: DNA
<213> ORGANISM: Artificial Sequence
<220> FEATURE:
<223> OTHER INFORMATION: Beta-actin Reverse primer (5 prime - 3 prime)

<400> SEQUENCE: 8
gactcatcgt actcctgctt gctg                                          24
```